(12) United States Patent
Gerhardt et al.

(10) Patent No.: US 8,802,088 B2
(45) Date of Patent: Aug. 12, 2014

(54) MIXTURE OF PEPTIDE-BOUND TRYPTOPHAN AND POLYPEPTIDE-BOUND TRYPTOPHAN

(75) Inventors: Cinderalla C. Gerhardt, Delft (NL); Luppo Edens, Rotterdam (NL)

(73) Assignee: DSM IP Assets B.V., Heerlen (NL)

( * ) Notice: Subject to any disclaimer, the term of this patent is extended or adjusted under 35 U.S.C. 154(b) by 446 days.

(21) Appl. No.: 12/989,869

(22) PCT Filed: Apr. 27, 2009

(86) PCT No.: PCT/EP2009/055038
§ 371 (c)(1),
(2), (4) Date: Jan. 14, 2011

(87) PCT Pub. No.: WO2009/133055
PCT Pub. Date: Nov. 5, 2009

(65) Prior Publication Data
US 2011/0110919 A1    May 12, 2011

(30) Foreign Application Priority Data
Apr. 29, 2008    (EP) .................................... 08155315

(51) Int. Cl.
| A61K 38/48 | (2006.01) |
| --- | --- |
| C12Q 1/34 | (2006.01) |
| C12Q 1/37 | (2006.01) |
| A61K 38/01 | (2006.01) |
| A61K 38/05 | (2006.01) |
| A61K 38/06 | (2006.01) |
| A61K 38/00 | (2006.01) |
| C07K 14/00 | (2006.01) |
| C07K 16/02 | (2006.01) |
| A61K 47/34 | (2006.01) |
| C12Q 1/06 | (2006.01) |
| G01N 33/68 | (2006.01) |
| A61K 38/47 | (2006.01) |
| A61K 38/02 | (2006.01) |
| A61P 25/00 | (2006.01) |

(52) U.S. Cl.
USPC ....... 424/94.61; 435/6.1; 435/7.23; 514/17.5; 514/17.6; 514/17.7; 514/772.3; 530/351; 530/391.1

(58) Field of Classification Search
USPC ............... 424/94.61; 435/6.1, 7.23; 514/17.5, 514/17.6, 17.7, 772.3; 530/351, 391.1, 399
See application file for complete search history.

(56) References Cited

U.S. PATENT DOCUMENTS

| 2006/0286252 A1 | 12/2006 | Rangavajla et al. |
| 2007/0207957 A1 | 9/2007 | Katayama et al. |
| 2009/0029005 A1 | 1/2009 | Van Amerongen et al. |
| 2011/0086803 A1 * | 4/2011 | De Roos et al. ............ 514/17.5 |
| 2011/0166085 A1 * | 7/2011 | Beck-Hoven Van et al. 514/21.9 |

FOREIGN PATENT DOCUMENTS

| CN | 101022737 A | 8/2007 | |
| EP | 1685764 A1 * | 8/2006 | ................ A23L 1/32 |
| EP | 1 757 289 | 2/2007 | |
| JP | 2003-321314 | 11/2003 | |
| JP | 2008-507270 | 3/2008 | |
| WO | WO 2006/009448 | 1/2006 | |

OTHER PUBLICATIONS

Mine et L., 2004. Antimicrobial Peptides Released by Enzymatic Hydrolysis of Hen Egg White Lysozyme. Journal of Agricultural and Food Chemistry, vol. 52, pp. 1088-1094.*
International Search Report for PCT/EP2009/055038, mailed Sep. 10, 2009.
Anonymous: "Muscle Milk—CytoSport", Internet Article [Online], (Feb. 9, 2008).
Anonymous: "Progain—Protein Energy Nutrition", Internet Article [Online], (Oct. 18, 2006).
Beulens, J.W.J. et al., "Alpha-Lactalbumin Combined with a Regular Diet Increases Plasma Trp-LNAA ratio", Physiology and Behavior, vol. 81, (Jan. 1, 2004), pp. 585-593.
Hunter, H.N. et al., "The Interactions of Antimicrobial Peptides Derived from Lysozyme with Model Membrane Systems", Biochimica et Biophysica Acta, Biomembranes, vol. 1668, No. 2, (Mar. 1, 2005). pp. 175-189.
Mine, Y. et al., "Antimicrobial Peptides Released by Enzymatic Hydrolysis of Hen Egg White Lysozyme", Journal of Agricultural and Food Chemistry, vol. 52, No. 5, (May 1, 2004), pp. 1088-1094.
CN Office Action dated Jun. 26, 2013 (first page only).
Polverino De Laurento et al; "Partly folded states of members of the lysozyme/lactalbumin superfamily: A comparative study by cicular dichroism spectroscopy and limited proteolysis," Protein Science, 11:2932-2946, Published by Cold Spring Harbor Laboratory Press, 2002.
Chinese Office Action dated Mar. 13, 2014, issued in connection with Chinese Patent Application No. 2009-80125142.8.

* cited by examiner

Primary Examiner — Jon P Weber
Assistant Examiner — Kailash C Srivastava
(74) Attorney, Agent, or Firm — Nixon & Vanderhye P.C.

(57) ABSTRACT

The present invention relates to a composition which comprises tryptophan whereby 10 to 90%, preferably 20 to 80% of the tryptophan is present as free tryptophan or peptide-bound tryptophan and 10 to 90%, preferably 20 to 80% of the tryptophan is present as polypeptide-bound tryptophan.

Figure 1:
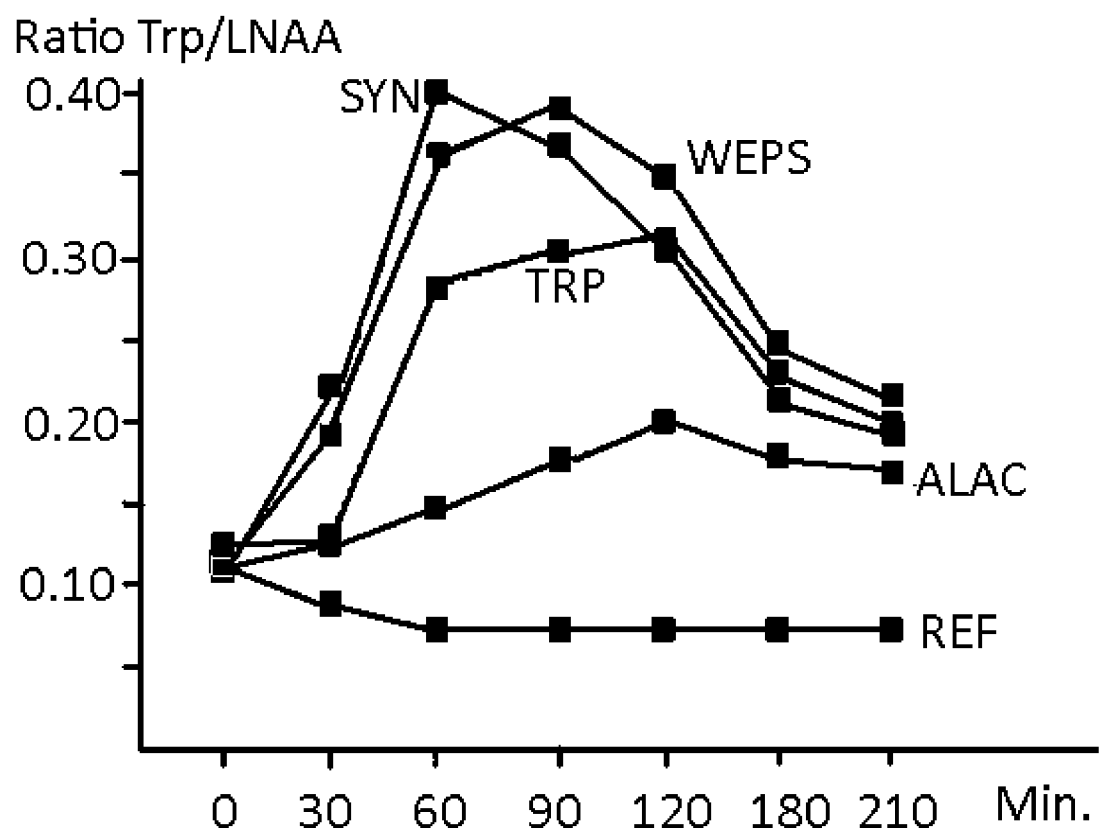

8 Claims, 10 Drawing Sheets though content of 5.3%, the tryptophan content of beta-lactoglobulin is only 2%. Whereas alpha-lactalbumine has a molar Trp/LNAA ratio of 0.11, beta-lactoglobulin has a molar Trp/LNAA ratio of not more than 0.04. So obviously any contamination of the alpha-lactalbumin preparation with beta-lactoglobulin, will dramatically lower the Trp/LNAA ratio of the final product.

MIXTURE OF PEPTIDE-BOUND TRYPTOPHAN AND POLYPEPTIDE-BOUND TRYPTOPHAN

This application is the U.S. national phase of International Application No. PCT/EP2009/055038 filed 27 Apr. 2009, which designated the U.S. and claims priority to EP Application No. 08155315.8 filed 29 Apr. 2008, the entire contents of each of which are hereby incorporated by reference.

FIELD OF THE INVENTION

The present invention relates to compositions which comprise tryptophan.

BACKGROUND OF THE INVENTION

Serotonine levels in the brain have been linked with mood, alertness, vigilance, sleep onset and quality, anxiolytic effects, depression, affective reaction control, appetite and sexual behavior. Many publications exist in which changes in brain serotonin levels are correlated with the availability of the natural amino acid L-tryptophan (Trp or W). Because of this correlation, methods to increase plasma tryptophan levels have received a lot of attention. Tryptophan quantities of around 1 gram/day per individual have been reported to yield clinically significant effects (Markus et al., Am. J Clin. Nutr 2005; 81, 1026-1033). One method to increase plasma tryptophan levels involves the consumption of protein preparations enriched in the whey protein alpha-lactalbumin. Alpha-lactalbumin preparations are readily available and have a relatively high tryptophan concentration. However, approaches in which the alpha-lactalbumine is provided as such, see for example DE 4130284 and JP 2279700, do not take into account that the main determinant of brain tryptophan and serotonin levels is not plasma tryptophan concentration alone, but the socalled Trp/LNAA ratio (Fernstrom and Wurtman. Science 1971, 173, 149-152). This Trp/LNAA ratio represents the molar ratio of tryptophan relative to the levels of Large Neutral Amino Acids (LNAA:, i.e. the sum of tyrosine, phenylalanine, leucine, isoleucine and valine) in plasma. These LNAA compete with tryptophan for uptake into the brain, presumably because the same transport mechanism across the blood-brain barrier is used. Therefore, the most effective way of increasing brain tryptophan concentrations is to supply preparations with a high Trp/LNAA ratio. A number of publications a.o. WO 02/46210, refer to the preparation of peptide fractions from alpha-lactalbumin having improved Trp/LNAA ratio's.

The use of free tryptophan, i.e. the free amino acid, would provide the simplest and cheapest approach to provide preparations with a high Trp/LNAA ratio. However, in many countries legislation exists that tightly regulates the supply of free tryptophan. The maximal allowable free tryptophan levels in its various application forms vary per country. To supply additional dietary tryptophan in a more natural way, more recent approaches aim at providing tryptophan rich proteins. As mentioned, alpha-lactalbumin as well as its hydrolysates have gained popularity as a safe option to enhance plasma tryptophan levels. However, the use of alpha-lactalbumin as a starting point for tryptophan-rich preparations, comes with disadvantages in terms of maximal Trp/LNAA ratios and costs. Alpha-lactalbumin and beta-lactoglobulin form the major protein constituents of whey. Because on an industrial scale a complete separation of alpha-lactalbumin and beta-lactoglobulin is difficult, the implication is that cost effective alpha-lactalbumin preparations will contain beta-lactoglobulin as well. Whereas alpha-lactalbumin has a molar tryptophan content of 5.3%, the tryptophan content of beta-lactoglobulin is only 2%. Whereas alpha-lactalbumine has a molar Trp/LNAA ratio of 0.11, beta-lactoglobulin has a molar Trp/LNAA ratio of not more than 0.04. So obviously any contamination of the alpha-lactalbumin preparation with beta-lactoglobulin, will dramatically lower the Trp/LNAA ratio of the final product.

In view of the broad interest in preparations that can modulate brain serotonine levels, there is a need for improved production methods for protein and peptide preparations having a high Trp/LNAA ratio that are broadly applicable in various food and neutraceutical products.

BRIEF DESCRIPTION OF THE INVENTION

The present invention relates to a process to produce a tryptophan-containing composition comprising bringing together, preferably mixing,
 a peptide-bound tryptophan composition, which is preferably water-soluble, and which has a Trp/LNAA ratio of more than 0.1, preferably of more than 0.15, and/or free tryptophan; and
 a polypeptide-bound tryptophan composition, which is preferably water-soluble, and which has a Trp/LNAA ratio of more than 0.15.

Preferably the peptide-bound tryptophan composition is obtained by hydrolyzing lysozyme, preferably hen egg lysozyme, to prepare a hydrolysate having a DH of between 5 and 45, and optionally fractionating, enriching or purifying the hydrolysate for example by removing part of the arginine or lysine containing peptides. Preferably the polypeptide-bound tryptophan composition is intact lysozyme, preferably hen egg lysozyme.

The present invention also relates to a composition which comprises tryptophan whereby 10 to 90%, preferably 20 to 80%, of the tryptophan is present as free tryptophan or peptide-bound tryptophan and 10 to 90%, preferably 20 to 80%, of the tryptophan is present as polypeptide-bound tryptophan. Optionally the composition comprises free tryptophan in addition to the peptide-bound tryptophan. In general less than 10% of the tryptophan present will be in free tryptophan form, preferably 0 to 5%, more preferably 0 to 2%, and most preferably 0 to 1% of the tryptophan present in the composition of the invention will be free tryptophan in case peptide-bound tryptophan is present as well. In general 0.1 to 20 g of the composition of the invention will be used in a dose for intake.

Preferably more than 30 mol %, preferably more than 40 mol %, more preferably more than 50 mol %, even more preferably more than 60 mol %, still more preferably more than 70 mol % and most preferably more than 80 mol % of the peptide-bound tryptophan is present in the form of a di- or a tripeptide. Moreover, preferably more than 40 mol %, more preferably more than 50 mol %, even more preferably more than 60 mol %, still more preferably more than 70 mol % and most preferably more than 80 mol % of the polypeptide-bound tryptophan is present as intact protein, preferably lysozyme.

Another aspect of the invention relates to the composition of the invention or lysozyme as a neutraceutical, preferably a medicament, or the use of the composition of the invention as a neutraceutical, preferably a medicament, or the use of the composition of the invention in the preparation of a neutraceutical, preferably a medicament, preferably whereby the neutraceutical, preferably a medicament, is used to prevent or to treat improving mood, cognition, appetite, alertness, vigilance, sleep onset and quality, anxiolytic effects, depression, affective reaction control or sexual behavior, or is used as ingredient in the preparation of a food, feed, dietary supplement.

Further the present invention relates to the use of lysozyme or the composition of the invention for intake to increase the plasma Trp/LNAA ratio over a period of time of between 15 and 240 minutes, preferably 30 and 240 minutes after consumption. This increase is compared to the plasma Trp/LNAA ratio just before the intake of the composition of the invention or lysozyme, or without the intake of the composition of the invention or lysozyme.

Advantageously, the composition of the invention also comprises carbohydrate.

DETAILED DESCRIPTION OF THE INVENTION

The present tryptophan-containing composition comprises two clearly distinguishable fractions which, upon oral intake, enable high Trp/LNAA ratios in blood plasma for prolonged periods. One fraction comprises peptide-bound tryptophan, and thus tryptophan-containing peptide, in the form of readily absorbable, low molecular weight peptides or free tryptophan. This fraction in case of tryptophan-containing peptide includes a large proportion of di- and tripeptides incorporating tryptophan. The other fraction comprises polypeptide-bound tryptophan, and thus tryptophan-containing polypeptide, preferably in the form of intact protein which, after oral intake, releases its peptide-bound tryptophan only very slowly. Therefore, the present application describes a novel combination of these two tryptophan-rich fractions that, upon oral consumption, rapidly evokes and maintains high Trp/LNAA levels in the blood for a prolonged time compared to using only the tryptophan-containing peptide fraction. The peptide-bound tryptophan present in the low molecular weight fraction is preferably derived from hen egg lysozyme, the polypeptide-bound tryptophan fraction or the larger molecular weight fraction is preferably lysozyme, for example intact hen egg lysozyme or another polypeptide-bound tryptophan source such as intact protein with a high Trp/LNAA ratio. Preferably the tryptophan-containing polypeptide is a protein that can resist proteolytic breakdown under stomach conditions. Advantageously such polypeptide-bound tryptophan such as intact protein, like intact lysozyme, can resist proteolytic breakdown under stomach conditions as described in the test for protease resistance (see Materials and Methods).

The readily absorbable, tryptophan-containing peptide fraction is preferably water-soluble, has preferably a DH higher than 15, more preferably a DH higher than 20, a Trp/LNAA ratio of more than 0.10, preferably more than 0.15, and preferably comprises the peptides AW (as dipeptide) or GNW (as tripeptide), more preferably AW and GNR. Examples of suitable tryptophan-containing peptide fraction are hydrolysates of lysozyme and alpha-lactalbumine, lysozyme hydrolysate is a preferred tryptophan-containing peptide fraction.

The polypeptide-bound tryptophan fraction providing the tryptophan at a slower pace typically has a DH below 10, preferably below 5. Intact protein has a DH of 0. The polypeptide-bound tryptophan fraction is preferably water-soluble. Moreover, the polypeptide-bound tryptophan fraction has a Trp/LNAA ratio of more than 0.15 and resists proteolytic breakdown under conditions prevalent in the human stomach. An in vitro test for the latter requirement is specified in the Materials & Methods section of the present application.

As mentioned before, the composition of the invention preferably comprises a carbohydrate to stimulate for example insulin production.

The present invention relates to a composition comprising free tryptophan or a peptide-bound tryptophan fraction as well as a polypeptide-bound tryptophan fraction. The peptide-bound tryptophan fraction has a molar Trp/LNAA ratio of at least 0.1, preferably of at least 0.15, and more preferably between 0.15 and 1.8 and comprises preferably at least one, preferably at least two different peptides, which are preferably water-soluble. Preferably this composition comprises AW (as dipeptide) or GNW (as tripeptide), preferably AW and GNW and most preferably AW and GNR, whereby the molar ratio of AW to GNW is between 1 to 2 and 10 to 1, preferably between 1 to 2 and 5 to 1. Moreover the tryptophan-containing peptides are rich in tryptophan and comprise at least one, preferably at least two different di- or tripeptides, whereby the peptide(s) selected from di- or tripeptides is/are present in an amount of at least 5 mol % of the total amount of di- and tripeptides, and in which composition more than 30 mol %, preferably more than 40 mol %, more preferably more than 50 mol %, even more preferably more than 60 mol %, still more preferably more than 70 mol % and most preferably more than 80 mol % of the peptide-bound tryptophan is present in the form of a di- or a tripeptide. The peptide-bound tryptophan fraction is preferably a lysozyme hydrolysate or a purified or fractionated lysozyme hydrolysate. We have found that this hydrolysate according to the invention quickly generates high blood plasma Trp/LNAA ratios in vivo. Quite surprisingly the Trp/LNAA ratios detected in blood plasma, were found to be higher than the Trp/LNAA ratio of the hydrolysate when given at a sufficiently high dose. A sufficiently high dose is preferably a dose of more than 10 grams, more than 12 grams or more than 14 grams of the lysozyme hydrolysate. Yet another advantage of this fraction is that the Trp containing peptides are very small so that even in combination with protein-rich products with less favorable Trp/LNAA ratios, the hydrolysate can immediately generate high blood plasma Trp/LNAA ratios. The composition of the invention may further comprise free tryptophan, for example free tryptophan may be added to the composition. Preferably this composition does not contain more than 1 wt % (on dry matter) of free tryptophan in case peptide-bound tryptophan is present.

Preferably the polypeptide-bound tryptophan fraction has a molar Trp/LNAA ratio of more than 0.15, preferably between 0.15 and 0.5, intact lysozyme has a Trp/LNAA ratio of 0.23. Upon its consumption, the polypeptide-bound tryptophan fraction also provides peptide-bound tryptophan but the peptide-bound tryptophan released in vivo from this polypeptide-bound tryptophan fraction becomes much later available for intestinal absorbtion than the peptide-bound tryptophan from the peptide-bound tryptophan fraction. Advantageously the intestinal absorption of peptide-bound tryptophan from the polypeptide-bound tryptophan fraction occurs thus later in time than the intestinal absorption of free tryptophan or peptide-bound tryptophan from the peptide-bound tryptophan fraction in case both fractions are consumed simultaneously. We have found that such a delayed tryptophan release can be achieved by the oral intake of intact proteins that resist enzymatic hydrolysis in the human stomach. Preferably such intact proteins have a high Trp/LNAA ratio.

According to another aspect of the invention the taste of a composition of hydrolysed lysozyme and (intact) lysozyme mixtures is improved compared to a composition comprising hydrolysed lysozyme without the (intact) lysozyme.

Another aspect of the invention is the use of lysozyme or a composition which comprises free tryptophan or a peptide-bound tryptophan fraction in combination with polypeptide-bound tryptophan and optionally carbohydrate for improving mood, premenstrual syndrome (PMS), cognition, alertness, vigilance, sleep onset and quality, anxiolytic effects, depression, affective reaction control or sexual behavior, or for use as ingredient in the preparation of a food, pet food, feed, dietary supplement or neutraceutical composition for mood, cognition, appetite, alertness, vigilance, sleep onset and quality, anxiolytic effects, depression, affective reaction control or sexual behavior. Apart from the free tryptophan or peptide-bound tryptophan, polypeptide-bound tryptophan and optionally carbohydrate, the composition may also comprise compounds recommended for "brain" nutrition, for relieving stress or depression or for improving alertness, mood, cognition or sleep patterns.

A food (including infant formula), pet food, feed, dietary supplement or neutraceutical composition is disclosed comprising the composition of the invention or produced according to the process of the invention or preferably the composition according to the invention comprising the peptides GNW (as tripeptide), SW (as dipeptide) or AW (as dipeptide) in combination with intact hen egg lysozyme.

According to a further embodiment the use is disclosed of the tryptophan-containing composition of the invention for increasing the Trp/LNAA ratio in plasma within 90 minutes, preferably 60 minutes, more preferably 30 minutes and most preferably 15 minutes after intake of the peptides or the composition, or for the preparation of a neutraceutical composition for increasing the Trp/LNAA ratio in plasma within 90 minutes, preferably 60 minutes, more preferably 30 minutes and most preferably 15 minutes after intake of the composition. According to yet another embodiment the use is disclosed of the tryptophan-containing composition of the invention for maintaining increased plasma Trp/LNAA ratios for periods beyond 90 minutes, preferably between 120 and 240 minutes, more preferably beyond 150 minutes after intake of the composition. According to an even further embodiment the use is disclosed of lysozyme or the tryptophan-containing composition of the invention for the preparation of a neutraceucal composition for maintaining increased plasma Trp/LNAA ratios for periods beyond 90 minutes, preferably between 120 and 240 minutes, more preferably beyond 150 minutes after intake of the composition.

The present invention provides a composition comprising tryptophan present as free tryptophan and/or in peptide-bound form which is very suitable for giving an effective increase of the Trp/LNAA ratio in plasma after a very short time interval and polypeptide-bound tryptophan for sustaining a high plasma Trp/LNAA ratio for a prolonged period of time compared to the stuation in which no polypeptide-bound tryptophan was present in the composition. This effect is especially noticeable at 90 to 240 minutes after intake of the composition of the invention. We noted that the two tryptophan comprising fractions in combination with carbohydrate contribute to the quick and prolonged Trp/LNAA increase.

According to one aspect of the invention the readily absorbable, peptide-bound tryptophan can be obtained from lysozyme, preferably hen egg lysozyme, by an enzymatic (pre-)hydrolysis in an industrial process i.e. (hen egg) lysozyme is preferably provided in the form of a hydrolysate. Offered in the form of a hydrolysate, the gastro-intestinal absorbtion of tryptophan-containing peptides is greatly facilitated. The polypeptide-bound tryptophan fraction is preferably represented by an intact protein with a high Trp/LNAA ratio that is not or only marginally degraded in the human stomach. Preferably this intact protein is hen egg's lysozyme. Alpha-lactalbumine from bovine milk, which is frequently used to raise Trp/LNAA blood ratio's, does not qualify as a suitable source of polypeptide-bound tryptophan as this molecule has a lower Trp/LNAA ratio than lysozyme. A composition according to the invention is characterized by a mixture of the readily absorbable free tryptophan and/or peptide-bound tryptophan such as lysozyme hydrolysate and the protease-resistant polypeptide-bound tryptophan such as an intact protein preferably lysozyme. Optionally the composition may comprise carbohydrate or free tryptophan. Preferably the composition of the invention is produced by mixing of free tryptophan and/or peptide-bound tryptophan preferably as hydrolysate and polypeptide-bound tryptophan preferably as intact protein such as lysozyme in weight ratios (measured as protein dry weight) ranging from 1:3 to 1:0.2. More preferably the composition comprises the hydrolysate and the intact protein in a 1:1 to 1:0.4 protein dry weight ratio. Both the readily absorbable and the protease-resistant protein fractions are characterized by molecular Trp/LNAA ratios higher than 0.10, preferably more than 0.15. The compositions may be provided as powders, liquids or pastes. These liquids or pastes may have neutral or acidic pH values. Preferably the mixtures have a pH value below 5, more preferably below 4.

In yet another embodiment of the present application, hen egg lysozyme is converted to a hydrolysate comprising a peptide composition of which more than 50 molar %, preferably more than 60 molar %, more preferably more than 75 molar % of the peptides present have a molecular weight below 500 Da. This with the proviso that the molecular weight distribution of the peptides present in the hydrolysate is carried out as described in the Materials & Methods section of the present application.

An important advantage of the readily absorbable fraction is that the tryptophan encompassed in free tryptophan or di- and tripeptides is transported across the intestine wall into the blood stream immediately after oral consumption. As a consequence, plasma tryptophan levels are increased almost instantaneously with a direct effect on brain serotonin levels. Data presented in Examples 6 and 11 of the present application show that the tryptophan residues presented in the form of such di- and tripeptides very quickly lead to high Trp/LNAA ratios. In this respect, the tryptophan residues presented in the form of these di- and tripeptides seem to be even more efficacious than free tryptophan. According to the present process a water-soluble peptide fraction is obtained having a molecular Trp/LNAA ratio of at least 0.10 preferably of at least 0.15 provided that the amino acid analysis of the hydrolysate is carried out as described in the Materials & Methods section of the present application.

Yet another important advantage of offering tryptophan in the form of di- and tri-peptides is that the gastro-intestinal uptake of these peptides is so fast, that they can be consumed in combination with protein containing foods, such as dairy products that naturally have a less favorable Trp/LNAA ratio, and yet lead to an effective increase of the Trp/LNAA ratio in the plasma within 90 minutes, preferably 60 minutes, more preferably 30 minutes period after consumption.

Therefore the present invention provides the use of lysozyme and/or the composition of the invention, for the use of obtaining an increased Trp/LNAA ratio in plasma within 90 minutes, preferably 60 minutes, most preferably 30 minutes after intake of the peptides or for the preparation of a neutraceutical composition for obtaining an increased Trp/LNAA ratio in plasma within 90 minutes, preferably 60 minutes, most preferably 30 minutes after intake of the peptides. Increased Trp/LNAA ratio in the present text means an increase of this ratio compared to the situation prior to the consumption or intake of the composition of the invention.

A "protein" or "polypeptide" is defined herein as a chain comprising more than 30 amino acid residues.

An "intact protein" or "intact polypeptide" is defined herein as a protein with a molecular weight identical to the naturally occurring protein if compared using the SDS-PAGE method described in the Materials & Methods section.

"Protease-resistancy" of an intact protein is determined as specified in the Materials & Methods section.

A "peptide" or "oligopeptide" is defined herein as a chain of at least two amino acids that are linked through peptide bonds. The terms "peptide" and "oligopeptide" are considered synonymous (as is commonly recognized) and each term can be used interchangeably as the context requires.

By peptide-containing tryptophan or tryptophan-containing peptide composition or fraction (fraction and composition are used interexchangeable in this context) is meant a composition which comprises at least one tryptophan-containing peptide. In the present text peptide-containing tryptophan or tryptophan-containing peptide composition may comprise only one peptide, preferably this composition comprises more than one peptide. By polypeptide-containing tryptophan or tryptophan-containing polypeptide composition or fraction (fraction and composition are used interexchangeable in this context) is meant a composition which comprises at least one tryptophan-containing polypeptide. In the present text polypeptide-containing tryptophan or tryptophan-containing polypeptide composition may comprise only one polypeptide.

A tryphophan containing-peptide means a peptide which comprises at least one tryphophan amino acid residue. A tryphophan containing-polypeptide means a polypeptide which comprises at least one tryphophan amino acid residue.

By peptide-bound tryptophan is meant tryptophan which is present as amino acid in a peptide. By polypeptide-bound tryptophan is meant tryptophan which is present as amino acid in a polypeptide.

The tryptophan-containing composition of the invention comprises a peptide-containing tryptophan composition and a polypeptide-containing tryptophan composition, and will thus comprise at least one tryptophan-containing peptide and at least one tryptophan-containing polypeptide.

Free tryptophan is meant tryptophan as free amino acid and thus not being part of a peptide or polypeptide.

A "water-soluble" peptide is a peptide which is soluble in water at a pH of 5.0.

All (oligo)peptide and polypeptide formulas or sequences herein are written from left to right in the direction from amino-terminus to carboxy-terminus, in accordance with common practice. The one-letter code of amino acids used herein is commonly known in the art and can be found in Sambrook, et al. (Molecular Cloning: A Laboratory Manual, $2^{nd}$ ed. Cold Spring Harbor Laboratory, Cold Spring Harbor Laboratory Press, Cold Spring Harbor, N.Y., 1989).

By protein hydrolysate, hydrolysate or hydrolysed protein is meant the product that is formed by enzymatic hydrolysis of the protein, an enriched or fractionated hydrolysate being a fraction of the protein hydrolysate for example enriched in selected peptides or wherein peptides or polypeptides have been removed from the hydrolysate. So an enriched hydrolysate is preferably a mixture of peptides (or a peptide mixture). The peptide mixture of the invention is therefore a mixture of at least two, preferably at least three, more preferably at least four tryptophan containing peptides. More preferably the mixture comprises a peptide composition of which more than 50 molar %, preferably even more than 60 molar %, and most preferably more than 75 molar % of the peptides present have a molecular weight below 500 Da. The Trp/LNAA ratio represents the molar ratio of tryptophan relative to the levels of other Large Neutral Amino Acids (LNAA:, i.e. the sum of tyrosine, phenylalanine, leucine, isoleucine and valine). Except for the plasma Trp/LNAA ratio, the Trp/LNAA ratio relates only to peptide-bound and/or polypeptide-bound amino acids. For the plasma Trp/LNAA ratio, the Trp/LNAA ratio relates to free amino acids. Thus free tryptophan, tyrosine, phenylalanine, leucine, isoleucine and valine are not taken into account in the Trp/LNAA ratio.

Peptide-bound amino acids are amino acids which are part of a peptide and not free amino acids.

The Tyr/BCAA ratio represents the molar ratio of tyrosine relative to the levels of branched chain amino acids (BCAA; i.e. the sum of leucine, isoleucine and valine). Preferably the Tyr/BCAA ratio is higher than 0.1, preferably higher than 0.12.

A favourable sleep onset and quality is defined as a quiet sleep entered into within 45 minutes after going to bed.

Mood is defined as the emotional state of mind and preferably measured using the Profile of Mood States questionnaire (see Example 6 of the present application).

Cognition is defined as the combined skills relating to such areas as problem solving, learning, memory and language.

Appetite is defined as the desire to eat, stimulated by feelings of hunger.

Alertness is defined as the attentive or vigilant state of mind, preferably measured using the Mackworth Clock Test and Critical Tracking Task (see Example 9 of the present application).

Anxiolytic effects are effects that result in relieving feelings of fear, apprehension or worry.

Depression is defined as a state of mind characterized by severe and persistant feelings of loss of pleasure.

The term sexual behavior is used herein as a synonym for libido.

In WO02/46210 a method for increasing the level of tryptophan in whey protein hydrolysates is described. In the method used, whey is first hydrolysed at acidic pH by one or more acid proteases, preferably by a pepsin, rennin, acid fungal protease, chymosin, papain, bromelain, chymopapain or ficin. The preferred incubation conditions are between pH 1.5 and 3.5 and were chosen to generate peptides having a hydrophobic nature. The hydrolysis is deliberately carried out in such a way that the tryptophan residues become incorporated in large, hydrophobic peptides. Much less tryptophan residues are present in the small, more water soluble peptides. In a subsequent processing step, the pH is raised to 4.0 to 6.0 to promote precipitation of these large, tryptophan-containing, peptides, hereby facilitating their selective recovery from the whey hydrolysate. Tryptophan is only present in relatively large peptides, the tryptophan uptake into the blood will be retarded hereby limiting the application possibilities of the preparation as a food or beverage ingredient, especially in combination with other proteins. Worthwhile to emphasize is that intact alpha-lactalbumine does not qualify as an intact protein fraction according to the invention, as it is not protease-resistant according to the test specified in the Materials & Methods section.

The present invention discloses a simple hydrolysis process, starting with a protein that is industrially available and is characterised by a high Trp/LNAA ratio. The present hydrolysis process has a tryptophan yield of more than 30% on protein tryptophan basis and generates a water soluble peptide composition comprising tryptophan. The fact that the larger part of the tryptophan residues is encompassed in di- and tripeptides, implies an immediate uptake into the blood stream. As will be disclosed, this property allows the incorporation of the hydrolysate in a larger variety of food or neutraceutical products. Quite surprisingly the present invention also discloses that upon oral consumption, the hydrolysate according to the invention can generate higher blood plasma Trp/LNAA ratios than the Trp/LNAA ratio of the actual hydrolysate.

According to the present invention hen egg lysozyme is used as a convenient starting material for the composition of the invention with a high Trp/LNAA ratio which, upon oral intake, leads to swift and long lasting increased Trp/LNAA ratios in the blood. Lysozyme is present in egg white in a concentration of 3-4%. By taking advantage of its exceptionally high isoelectric point, lysozyme is industrially isolated from egg white using a simple cation chromatographic purification step optionally followed by a crystallisation step. The resulting product is almost pure and this industrially available product has a molecular tryptophan content of 7.8% and molecular Trp/LNAA ratio of at least 0.15. Thus lysozyme, i.e. intact protein, has a Trp/LNAA ratio that is significantly higher than pure alpha-lactalbumin and/or beta-lactoglobulin. Therefore, the lysozyme hydrolysates according to the present invention has preferably a molar Trp/LNAA ratio which is higher than 0.15, more preferably the Trp/LNAA ratio is higher than 0.20, even more preferably the Trp/LNAA ratio is higher than 0.23, still more preferably the Trp/LNAA ratio is higher than 0.25 and most preferably the Trp/LNAA ratio is higher than 0.30. In general the molar Trp/LNAA ratio is below 3.0. As such lysozyme presents a preferred starting point for tryptophan-containing peptides or compositions and can be used as polypeptide-bound tryptophan composition. Lysozyme (EC 3.2.1.17) is an enzyme able to hydrolyse specific peptidoglycan bonds in bacterial cell walls leading to cell lysis. Because of its bactericidal effect, lysozyme plays an important role in host defence by preventing infections. Under physiological conditions, the lysozyme molecule is very resistant to proteolytic attack. This unusual resistance can be explained on evolutionary grounds: as invading bacteria are able to excrete a large variety of proteases, a lysozyme molecule susceptible to such proteases would be rapidly inactivated. Its protease resistancy has been illustrated for a.o. stomach lysozymes of ruminants (Dobson et al, J. Biol Chem. 1984, 259 (18)11607-11616). From a structural point of view, the presence of four disulphide bonds in the molecule can be expected to add to the protease resistancy of lysozyme. On the basis of data presented in Example 1 of the present application, hen egg lysozyme can be considered so resistant to proteolytic attack, that it is unlikely that the molecule can be efficiently digested in the proximal part of the human intestinal tract. The consequence of this protease resistancy is that, despite its very attractive Trp/LNAA ratio, intact lysozyme is not a suitable source for quickly raising plasma tryptophan levels simply because the tryptophan residues are not easily liberated under the physiological conditions existing in the gastro-intestinal tract. However, intact hen egg lysozyme can be enzymatically hydrolysed under near neutral pH conditions (Porter et al., J. Agric. Food Chem. 1984, 32, 334-339). This article is in line with our observation that intact hen egg lysozyme will be able to release peptide-bound tryptophan in the more distal parts of the human intestine. Together with the above described readily absorbable, "pre-digested" lysozyme hydrolysate, this opens the unexpected possibility of creating a preparation which, upon oral intake, leads to an immediate surge of the Trp/LNAA ratio in the plasma followed by a slow and sustained release of peptide bound Trp. These kinetics are reproduced in the Trp/LNAA levels in the plasma leading to new and surprising effects on serotonine as well as dopamine in the brain.

Upon dietary intake, proteins present in food are gradually hydrolysed to smaller fragments and then transported across the wall of the small intestine and taken up into the blood. In the gastro-intestinal tract a number of different proteases that originate in the stomach, pancreas and small intestine are active to hydrolyse dietary proteins. Endoproteases such as pepsin, trypsin and chymotrypsin cleave dietary proteins into smaller oligopeptides. Of these endoproteases only pepsin is active in the acid surroundings of the stomach. Trypsin and chymotrypsin become active in the near neutral surroundings prevalent in the duodenum, jejunum and the more distal parts of the intestine. The oligopeptides formed by these endoproteases are then further hydrolysed by a number of other enzymes such as di- and tripeptidyl peptidases to yield di- and tripeptides and by amino- and carboxypeptidases to yield free amino acids. Carrier systems specific for the transport of free amino acids or di- and tripeptides are responsible for an efficient transport across the intestine wall into the blood stream. Upon dietary intake, free amino acids, di- and tripeptides become immediately incorporated in the blood stream. Peptides larger than tripeptides require additional enzymatic cleavage to enable uptake.

We have found that the tryptophan-containing composition of to the invention is also effective if incorporated into high protein containing food matrices as presented by, for example, dairy products. This is quite surprising as protein containing food matrices represent high LNAA loads and thus can be expected to reduce the effect of products with high Trp/LNAA ratios. A possible explanation for this unexpected phenomenon is that the usual food products incorporate intact, rather than extensively hydrolyzed proteins. A typical size distribution of a hydrolysate according to the invention is presented in FIG. 3. According to this Figure, the majority of the tryptophan and tyrosine incorporating peptides has a molecular weight below 500 Da. In view of the very high molecular weight of tryptophan (MW=186) and tyrosine (MW=163) and the fact that only very low levels of free tryptophan are present, the implication is that the majority of these peptides will be tri- or di-peptides. As tryptophan has a much higher molar absorptivity than tyrosine at the wavelength used, peak values will refer to tryptophan incorporating peptides mainly.

Because the tryptophan containing di- and tripeptides present in the tryptophan-containing composition according to the invention are absorbed so much faster than, for example, the large quantity of LNAA's presented by non-hydrolyzed matrix proteins, we assume that this is the reason that even in the presence of large quantities of matrix proteins, high plasma Trp/LNAA ratios can be obtained.

Particular situations require high plasma Trp/LNAA ratios for extended periods of time. For example to improve and extend the sleeping time or situations requiring enhanced cognitive performance for long periods. Also situations that require mood improvement such as has been described for cases of premenstrual syndrome or post-menopausal women the compositions according to the present invention are of particular relevance. Whereas the peptide-bound tryptophan such as the lysozyme hydrolysate will yield an almost instant increase of the plasma Trp/LNAA ratio, the slow digestion of polypeptide-bound tryptophan, such as the pepsin resistant protein with its high Trp/LNAA ratio, will guarantee a continued release of peptide-bound tryptophan in the more terminal parts of the human intestine resulting in increased Trp/LNAA ratio in the plasma in the period between 120 and 240 minutes after the intake of the composition of the invention.

Interestingly, our present experimental data also seem to indicate that the hydrolysate according to the invention can generate Trp/LNAA ratios in the blood of human volunteers that are higher than the Trp/LNAA ratio of the hydrolysate when given at a sufficiently high dose. A sufficiently high dose is preferably a dose of more than 10 grams, more than 12 grams or more than 14 grams of the lysozyme hydrolysate. Although such a phenomenon is unknown and there exists, according to our best knowledge, no accepted explanation for this effect, we believe that this may be caused by the extremely high arginine content of the lysozyme molecule. The presently posed working hypothesis is disclosed herein to explain the experimental data shown in the Examples. This hypothesis is used to give the present insight of the inventors but the present invention is no way linked or limited to this hypothesis. So the present invention stands independent of the correctness of the hypothesis. An increase in blood insulin stimulates the uptake of amino acids from blood into peripheral tissue, especially muscle. However, tryptophan largely escapes this route due to the fact that in blood, tryptophan is bound to the plasma protein albumin. As a consequence, increased insulin levels decrease the concentrations of LNAA, but not tryptophan, thus increasing the Trp/LNAA ratio in blood. Since carbohydrate ingestion elicits insulin secretion and stimulates the uptake of LNAA in periferal tissues and notably muscles, plasma Trp/LNAA ratio's are increased by carbohydrate intake (Fernstrom and Wurtman, 1972, Metabolism, Vol. 21, No. 4, 337-342). Apart from carbohydrate ingestion, insulin secretion is also known to be stimulated by particular amino acids. If plasma amino nitrogen levels resulting from infusion of the individual amino acids are very similar, the insulin responses vary considerably. Floyd et al (J Clin Invest 45(9):1487-502), established a decreasing insulin response for the amino acids arginine>lysine>leucine>phenylalanine>valine>methionine. In view of the fact that lysozyme is particularly rich in the amino acid arginine, it is tempting to speculate that an insulin stimulating effect triggered by arginine leads to the high Trp/LNAA ratios.

Because carbohydrates are known for their insulin stimulating effect, the hydrolysates according to the present invention are preferably formulated in combination with carbohydrates. In conjunction with the presence of fast absorbable peptide-bound tryptophan and slow absorbable polypeptide-bound tryptophan, the preferred compostion according to the present invention comprises carbohydrate.

Figure 3:
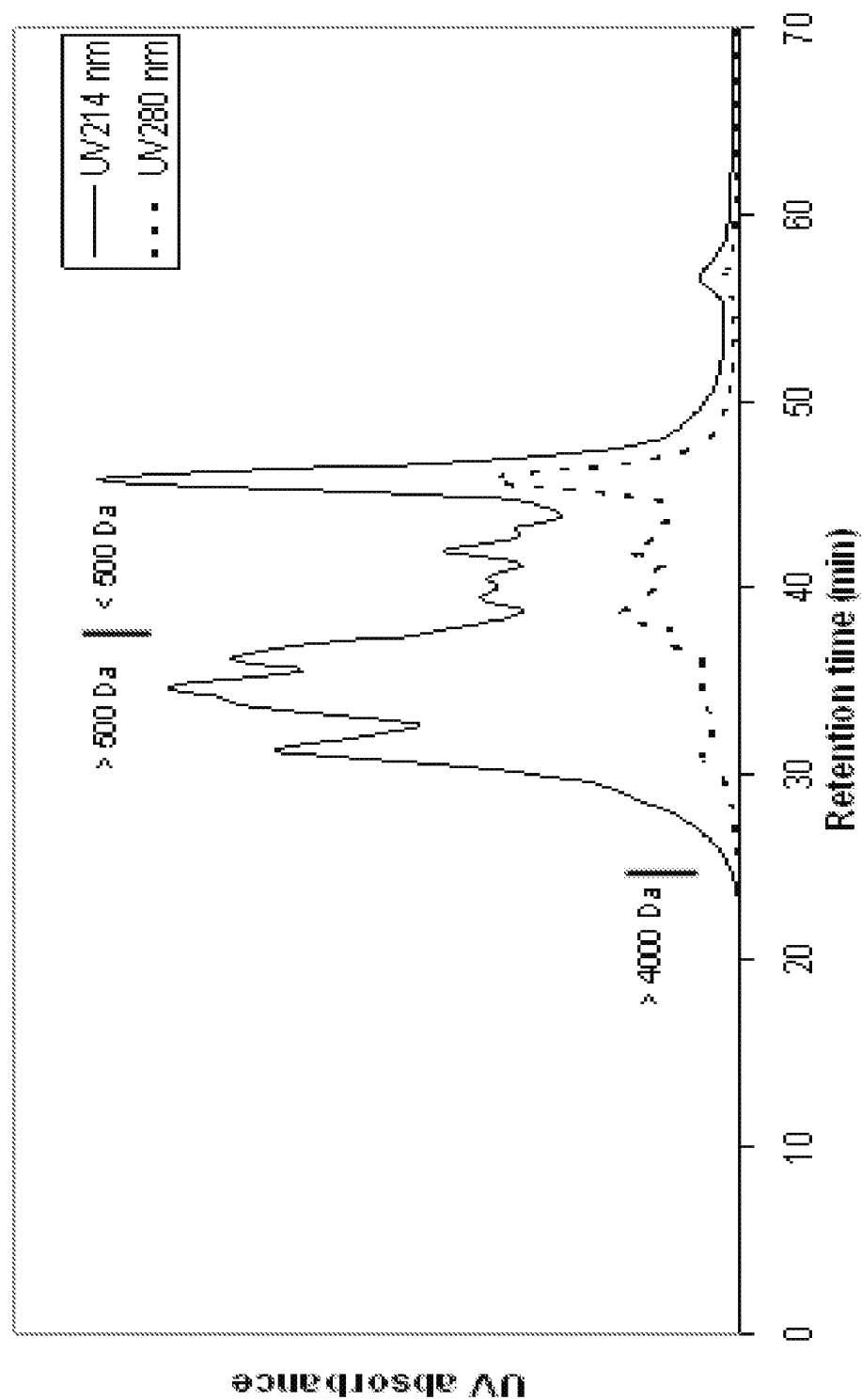

In one embodiment of the present invention, lysozyme, preferably hen egg lysozyme is enzymatically (pre-)hydrolysed in an industrial process i.e. the (hen egg) tryptophan-containing peptide composition is preferably provided in the form of a hydrolysate or an enriched hydrolysate. Offered in the form of such an (enriched) hydrolysate, the intestinal absorbtion of tryptophan containing peptides is greatly facilitated. In another embodiment of the present application, hen egg lysozyme is converted to a hydrolysate or enriched hydrolysate comprising a tryptophan comprising peptide population of which more than 50 molar %, preferably more than 60 molar %, more preferably more than 75 molar % of the peptides present have a molecular weight below 500 Da. Preferably such an (enriched) hydrolysate does not contain more than 1 wt % (on dry matter) of free tryptophan. The molecular weight analysis of the tryptophan comprising peptides present in the hydrolysate is carried out as described in the Materials & Methods section of the present application and is illustrated in FIG. 3. An important advantage of the latter embodiment is that the tryptophan encompassed in di- and tripeptides is transported across the intestinal wall into the blood stream immediately after oral consumption. As a consequence, plasma tryptophan levels are increased almost instantaneously with a direct effect on brain serotonin levels. Quite surprisingly the data presented in Example 6 of the present application show that the efficacy of the tryptophan residues presented in the form of these di- and tripeptides is even more efficacious than free tryptophan. This observation emphasizes the advantages offered by the present invention.

WO 2006/009448 provides protein hydrolysates obtained from hen egg proteins having antihypertensive properties, as well as food products and food supplements comprising these hydrolysates. This document divulges the preparation of a large number of hydrolysates, including those obtained from hen egg lysozyme. All these hydrolysates aim at reducing blood pressure or preventing blood pressure rises upon oral ingestion in humans. WO 2006/009448 also describes the preparation of lysozyme hydrolysates obtained under alkaline conditions using subtilisin (EC3.4.21.62; commercial names Alcalase or Protex). According to the high degrees of hydrolysis that are obtained, these lysozyme hydrolysates contain a large proportion of peptides with a molecular weight below 500 Da. However, nowhere in the text of WO 2006/009448 reference is made to the fact that lysozyme is a protein source having a high tryptophan content that can positively affect brain serotonin levels. Also not mentioned is that lysozyme hydrolysates comprise water-soluble peptides incorporating a high amount of tryptophan and a relatively low amount of LNAA. WO 2006/009448 also does not mention the high arginine and lysine content of either lysozyme or lysozyme hydrolysates. We have found that on the basis of the data presented in the present application, the high tryptophan content of the lysozyme molecule in combination with the ubiquitous presence of arginine and lysine makes lysozyme the perfect starting material for an in vivo generation of high Trp/LNAA ratios. Furthermore the text of WO 2006/009448 does not mention the advantages offered by the hydrolysate used in the present invention in its co-consumption with other protein containing foods. Apart from the use of membrane filters, the text of WO 2006/009448 also does not mention methods to obtain peptide fractions from these hydrolysates having selected amino acid compositions or using specific methods to increase tryptophan contents or to increase Trp/LNAA ratios. Furthermore the advantage of offering a highly degraded lysozyme hydrolysate in combination with a non-degraded, intact lysozyme is not recorded.

The data presented in Example 4 of the present application, indicate that the lysozyme hydrolysate obtained by incubating lysozyme at an alkaline pH with subtilisin is particularly rich in the Ala-Trp (AW) dipeptide. This finding suggests that a chemically synthesized AW dipeptide could provide a suitable alternative for the present lysozyme hydrolysate. Although the use of a synthetic dipeptide has obvious legislative drawbacks, important advantages are its cost effectiveness and its ideal Trp/LNAA ratio. Theoretically, twenty different tryptophan containing dipeptides are available, but our investigations have shown that the dipeptides Ala-Trp (AW) and Ser-Trp (SW) represent particularly preferred options to enhance plasma Trp/LNAA ratios via a synthetic dipeptide. Production of the AW and SW dipeptides via chemical synthesis is possible using conventional techniques as for instance described in "Peptides: Chemistry and Biology" by N. Sewald and H. D. Jakubke, Eds. Wiley-VCH Verlag GmbH, 2002, Chapter 4. Particular cost-effective methods of chemical peptide synthesis suitable for large-scale production are based on the use of alkylchloroformates or pivaloyl chloride for the activation of the carboxylic group combined with the use of methyl esters for C-terminal protection and benzyloxycarbonyl (Z) or tert-butyloxycarbonyl groups for N-protection. A detailed procedure for a cost effective synthesis of dipeptide SW is provided in Example 5. The combination of such a chemically synthesized tryptophan-containing dipeptide in combination with a polypeptide-bound tryptophan such as a pepsin-resistant protein with a high Trp/LNAA ratio, preferably intact lysozyme, is new.

Having the composition according to the present invention available, other new and surprising applications are envisaged which have technical and economical advantages.

A new use would be the incorporation of lysozyme and/or the composition of the invention in various infant formula products. Cow's milk contains 20% whey protein and human milk 40 to 60%. As a consequence, cow's milk contains less alpha-lactalbumin and thus tryptophan as human milk. Normal, full-term infants are usually fed cow's milk based formulas, products that do not provide an amino acid profile equivalent to that of mother's milk. Although the consequences of an insufficient tryptophan supply are not fully known, infant formula products high in tryptophan, may have benificial effects on conscious behaviour and sleep onset and quality of the infant. A strong indication that a high plasma tryptophan level promotes a quick onset of a quiet sleep in healthy newborns was provided by Yogman and Zeisel in N Engl J Med. 1983 Nov. 10; 309(19):1147-1149. Accordingly, the present invention provides compositions for infant formula products in which the tryptophan level has been raised.

According to another aspect of the invention the composition according to the invention can be used in meal replacement products. For example, WO 2005/023017 describes the advantages of gelatin in high dosages as a suitable component in meal replacement products. While providing excellent organoleptic properties, the gelatin does not provide the required amino acid balance, for example, it does not incorporate the essential amino acid tryptophan. So in order to arrive at a composition having the proper balance of amino acids as required by EC Directive 96/8/EC, tryptophan has to be added to such gelatin comprising compositions. In WO 2005/023017 tryptophan is preferably added in the form of tryptophan-rich protein, e.g. egg white powder or whole egg powder. We have now found that the tryptophan containing composition according to the present invention offer an improved solution to this problem as these hydrolysates supply tryptophan in a much more concentrated form. Moreover, lysozyme itself contains all essential amino acids at the required amount, and as such is a nutritionally complete protein that ideally fits in a meal replacer.

According to yet another aspect of the invention, lysozyme and/or the composition according to the invention are used to improve sleep onset and quality in infants, children and adults. Sleep problems are very prevalent among individuals belonging to various age groups and are associated with medical disorders. The tryptophan-containing composition according to the present invention are useful to treat sleep problems in general but they present a useful tool to overcome problems connected with cognitive, psychological, social and behavioural disturbances. Examples are the establishment of a good sleep hygiene, overcoming a sleep-onset association or a circadian rythym sleep disorder. The products also can be useful in improving sleep onset and quality and mental state of, for example, fibromyalgia patients. Fibromyalgia syndrome is a chronic pain syndrome that is related to severely disturbed sleep onset and quality and emotional stress. We have found that a regular intake of the composition according to the invention and/or lysozyme improves the sleep onset and quality of individuals suffering from sleep problems in general.

The composition according to the present invention offer additional advantages such as the supply of (semi-) essential, amino acids. Lysozyme has not only a high tryptophan level but incorporates a significant number of tyrosine residues as well. Tyrosine is the precursor for the neurotransmittor dopamine and it is known that plasma tyrosine levels affect the dopamine levels in the brain. Lysozyme hydrolysate contains not only less LNAA's than other known high-tryptophan peptides, it also contains less branched-chain amino acids (BCAA's) than other known high-tryptophan peptides. This is important since BCAA's are known to lower the plasma availability of the dopamine precursor tyrosine. So, its high Trp/LNAA ratio in combination with its high Tyr/BCAA ratio, makes lysozyme a unique molecule. Therefore, the composition according to the invention comprising lysozyme hydrolysate and intact lysozyme is very well placed as a "brain food", that is, for the supply of the essential amino acids required for proper neurotransmittor levels. The dopamine system is known for its critical role in mediating reward and motivation and its effects on concentration, memory, alertness, attention, problem solving and psychomotor coordination. As illustrated in Example 9 of the present application, the intake of the lysozyme hydrolysate according to the invention has significant beneficial effects on vigilance, alertness, concentration and psychomotor coordination. This finding demonstrates that the composition according to the invention can be expected to stimulate not only the serotonine system, but also the dopamine system.

Several groups of individuals can benefit from this finding. For example, women during their menopausal years have general complaints about their reduced capability for problem solving which they relate to an inability to concentrate. Therefore, the composition according to the invention is especially suited to fight these problems in women of this age group. In the category of young and middle-aged women, the premenstrual syndrome is quite common. The syndrome is characterized by a wide variety of symptoms, but complaints about depression and mood lability are frequently occurring. To fight such complaints, selective serotonin reuptake inhibitors such as fluoxetine are frequently prescribed and, in women with milder symptoms, dietary adaptations and prevention of stress are recommended. On the basis of the outcome of the experiments described in Examples 6 and 9 of the present application, the composition according to the invention presents an excellent treatment for, especially such milder cases. Furthermore, insufficient dopamine is associated with the attention-deficit hyperactivity disorder (ADHD) so that the symptoms of this disorder can be expected to be aleviated by the composition according to the invention. Our findings that the beneficial effects on post-stress performance are especially prominent in stress-resistant subjects is surprising. A possible explanation may be that stressed people, with an (over-)active serotonin system, need tryptophan from the drink to replenish their serotonin stores and thus cannot use this tryptophan for improving their performance in the tasks. According to that line of reasoning, stress-resistant people without an overactive serotonergic system do not need tryptophan to replenish their serotonin stores and can use it to improve their post-stress performance. An alternative explanation may be that these effects are in fact due to a stimulatory effect of dopaminergic processes. Dopamine synthesis can be enhanced by food ingredients rich in tyrosine, particularly if combined with low levels of branched-chain amino acids (BCAAs). These working hypotheses are disclosed herein to explain the experimental data shown in the Examples and are used to give the present insight of the inventors. However, the present invention is no way linked or limited to these hypotheses. So the present invention stands independent of the correctness of these hypotheses. As stated elsewhere, lysozyme has not only a high tryptophan level but incorporates a significant number of tyrosine residues as well.

Lysozyme and/or the composition according to the present invention also raises the cysteine content in food products. Although not an essential amino acid, cysteine concentrations are limiting in many food products. The endogeneous synthesis of cysteine requires the presence of methionine and, like cysteine, methionine concentrations are limiting in many food products. The advantages of an increased cysteine content of foods relate amongst others to the an antagonistic effect on the serum homocysteine elevating effect of methionine. This finding has been described in WO 03/055335. The composition according to the invention are also characterized by a high cysteine level. In fact, the lysozyme molecule contains even more cysteine residues (8) than tryptophan residues (6). In this respect the composition according to the present invention form an excellent source for increasing the cysteine content of certain products. Increased cysteine contents are found to be important for products such as infant formula. Not only infant formula based on casein or mixtures of casein and whey proteins but also for soy based products and in fact for all protein rich products in which the main source of the protein is provided by a protein containing relatively low amounts of tryptophan or cysteine. Apart from the protein components from bovine milk and gelatin, maize protein, yeast protein, pea protein, soy protein and rice protein represent examples of such proteins. Furthermore, the above mentioned meal replacement products containing high dosages of gelatin contain inadequate amounts of cysteine.

Lysozyme and/or the composition according to the present invention which comprises for example a di- or tripeptide, which comprise tryptophan, especially SW (as dipeptide) or AW (as dipeptide), can be used in any suitable form such as a food or a beverage, as Food for Special Nutritional Uses, as a dietary supplement, as a neutraceutical or even in feed or pet food. The lysozyme containing composition may be added at any stage during the normal process of these products. If used in food or beverages, products with a relatively low protein content are preferred in order to maintain the high Trp/LNAA ratio in blood after consumption of the products according to the invention. Relevant food products include e.g. cereal bars, chocolate and chocolate containing drinks, bakery items such as cakes and cookies and also liquid foods such as soups or soup powders. Apart from dairy products such as milk and yogurt, other suitable beverages encompass non-alcoholic and alcoholic drinks as well as liquid preparations to be added to drinking water and liquid food. Non-alcoholic drinks are preferably mineral water, sport drinks, fruit juices, lemonades, teas, coffee, decaffeinated coffee, concentrated drinks such as shots, energy drinks (for example drinks containing glucuronolactone, caffeine or taurine) and carbonated beverages (for example pops, sodas and cola drinks).

Preferred combinations with lysozyme and/or the composition according to the invention are with compounds recommended for "brain nutrition" such as iron, zink, magnesium, vitamins (especially B2, B6, folic acid and C), omega-3 and DHA fats or fatty acids, glucose, GABA, choline, phosphatidyl serine, co-enzyme Q10, creatine, taurine and 5-HTP, or with compounds recommended for relieving stress or depression such as valerian, chocolate, St John's worth, 5-HTP, phosphatidyl serine, alcohol, lemon balm, green tea or green tea extracts, chamomile or S-adenosyl methionine, or with compounds recommended for improving alertness such as caffeine, guarana, ginseng, gingko bilboa, St John's worth, and 5-HTP or with compounds recommended for mood improvement such as GABA, 5-HTP, PEA, chocolate, green tea or green tea extracts, gingko bilboa, Salvia or S-adenosyl methionine or with compounds recommended for improving sleep such as milk peptides, free tryptophan, opoid peptides or melatonin. Examples of Foods for Special Nutritional Uses include the categories of sport foods, slimming foods, infant formula and clinical foods. The term dietary supplement as used herein denotes a product taken by mouth that contains a compound or mixture of compounds intended to supplement the diet. The compound or mixture of compounds in these products may include: vitamins, minerals, herbs or other botanicals and amino acids. Dietary supplements can also be extracts or concentrates, and may be found in many forms such as tablets, capsules, softgels, gelcaps, liquids, or powders.

The tryptophan containing composition of the invention and/or lysozyme can also be used as or in a neutraceutical compostion or in the preparation of a neutraceutical. The term neutraceutical as used herein denotes the usefulness in both the nutritional and pharmaceutical field of application. Lysozyme and/or the neutraceutical compositions according to the present invention may be in any form that is suitable for administrating to the animal body including the human body, especially in any form that is conventional for oral administration, e.g. in solid form such as (additives/supplements for) food or feed, food or feed premix, tablets, pills, granules, dragées, capsules, and effervescent formulations such as powders and tablets, or in liquid form such as solutions, emulsions or suspensions as e.g. beverages, pastes and oily suspensions. Controled (delayed) release formulations incorporating the hydrolysates according to the invention also form part of the invention. Furthermore, a multi-vitamin and mineral supplement may be added to the neutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

In a preferred aspect of the present invention lysozyme and/or the composition may be used as a neutraceutical or nutritional supplement, e.g. for mood improvement or for the improvement of cognitive functions such as learning, memory, vigilance and alertness for example in elderly people, but also younger people such as students who are preparing exams and for persons playing, for example, computer or internet games. As mentioned before, for pre- and post menopausal women lysozyme and/or the composition according to the invention are of particular relevance. Lysozyme and/or the composition according to the invention are also of particular relevance for sports people; both professional athetes with demanding training schemes, as well as recreational sports people such as people playing tennis or golf. This means that the present invention relates to the use of the hydrolysates according to the invention as given above and as "condition improver", i.e. as means to reduce irritability and tiredness (eventually reducing the risk for overtraining), to reduce or prevent or alleviate physical and mental fatigue, to favour undisturbed sleep, that is to act against insomnia and sleep disorders and to improve sleep, and to increase energy in more general terms, especially to increase the brain energy production, in diseased or normal healthy individuals. Moreover for cognition improvement in general, and especially for maintenance or improvement of attention and concentration, of the memory and of the capacity for remembering, of the learning ability, of the language processing, of problem solving and of intellectual functioning; for improvement of the short-term as well as long-term memory; for increasing the mental alertness; for enhancing the mental vigilance; for reducing the mental fatigue; for supporting cognitive wellness, for maintaining balanced cognitive function. If required for obtaining cost effective preparations with a high Trp/LNAA ratio, the hydrolysates according to the invention optionally comprise free tryptophan.

LEGENDS TO THE FIGURES

FIG. 1 The molar Trp/LNAA ratio in plasma as a function of time after consumption of the products detailed in Example 6. REF=casein hydrolysate, ALAC=intact alpha-lactalbumin, Trp=free tryptohan, WEPS=tryptophan-enriched lysozyme hydrolysate, SYN=synthetic dipeptide Ser-Trp.

Figure 2:
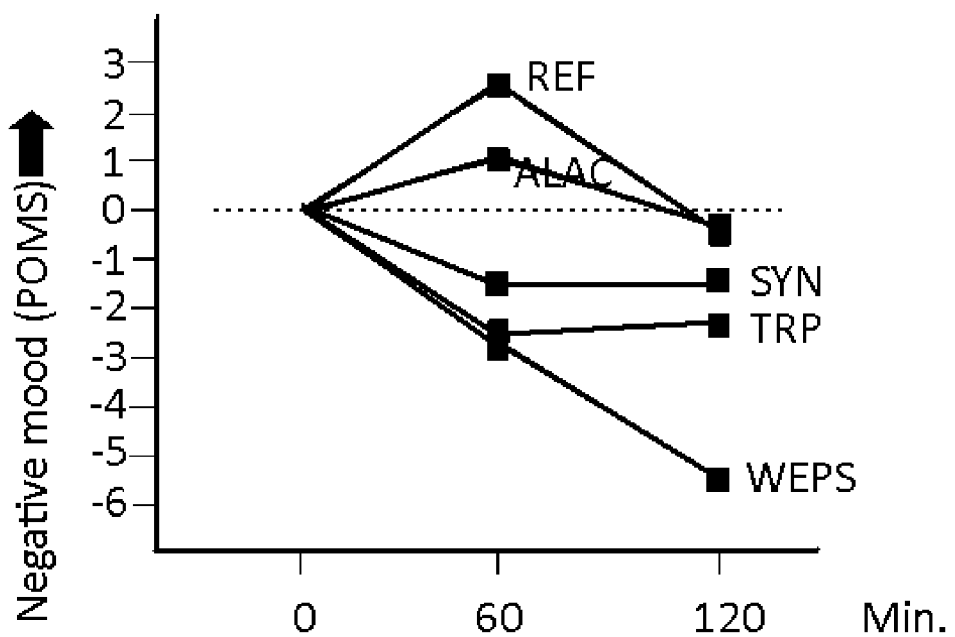

FIG. 2 Negative mood (as measured with the Profile of Mood States test (POMS)) as a function of time after consumption of products detailed in Example 6. REF=casein hydrolysate, ALAC=intact alpha-lactalbumin Trp=free tryptohan, WEPS=tryptophan-enriched lysozyme hydrolysate, SYN=synthetic dipeptide Ser-Trp.

FIG. 3 Size distribution of the water-soluble peptide fraction of a lysozyme hydrolysate. Using the method for determining molecular weight distribution of peptides and proteins present in hydrolysates as detailed in the Materials and Methods section, a lysozyme hydrolysate prepared according to the method described in Example 3 was analyzed. Absorbancy measurements at 214 nm record the presence of peptide bonds. Absorbancy measurements at 280 nm record the presence of the aromatic side chains of tryptophan and tyrosine. As tryptophan has a much higher molar absorptivity than tyrosine at this wavelength, peak values will refer to tryptophan incorporating peptides mainly.

Figure 4:
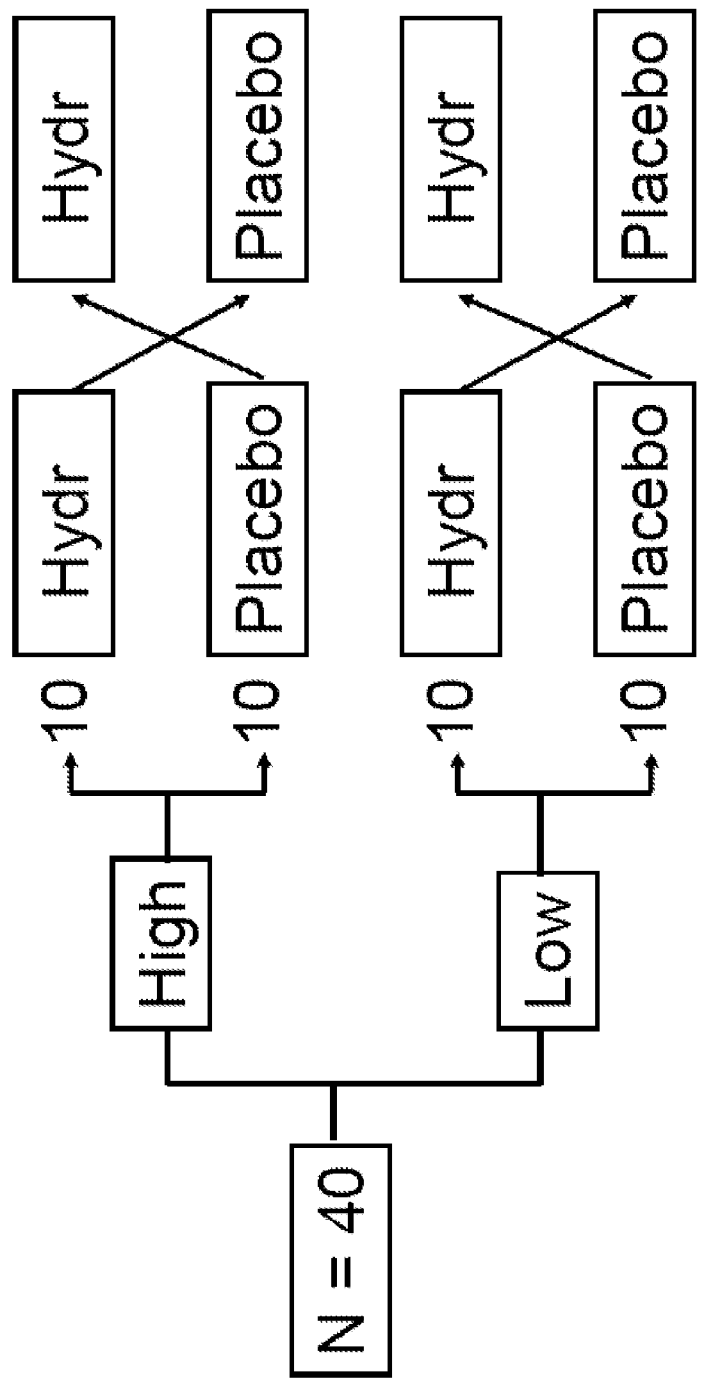
Figure 5:
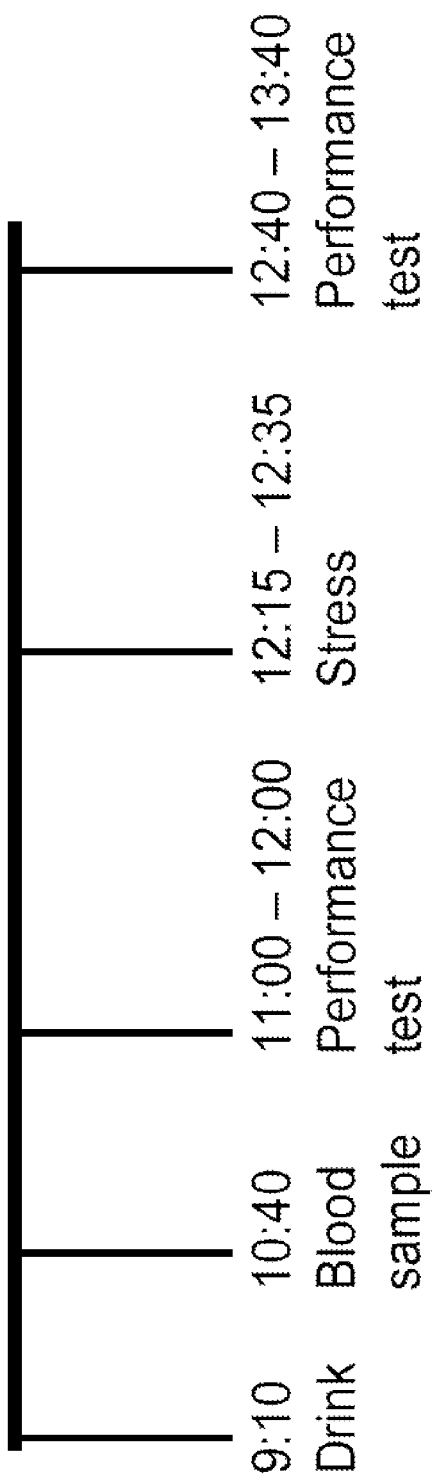

FIG. 4. Flow diagram of the study design of the experiment described in Example 9. High: stress-susceptible volunteers; low: stress-resistant volunteers; hydr::Trp-rich lysozyme hydrolysate; placebo: casein hydrolysate FIG. 5. Flow diagram of a typical study day of the experiment described in Example 9. Drink: consumption of drink containing Trp-rich hydrolysate or placebo; blood: blood sampling for assessment of plasma amino acid levels; performance: performance tests before and after uncontrollable stress; stress: arithmetic task.

Figure 6:
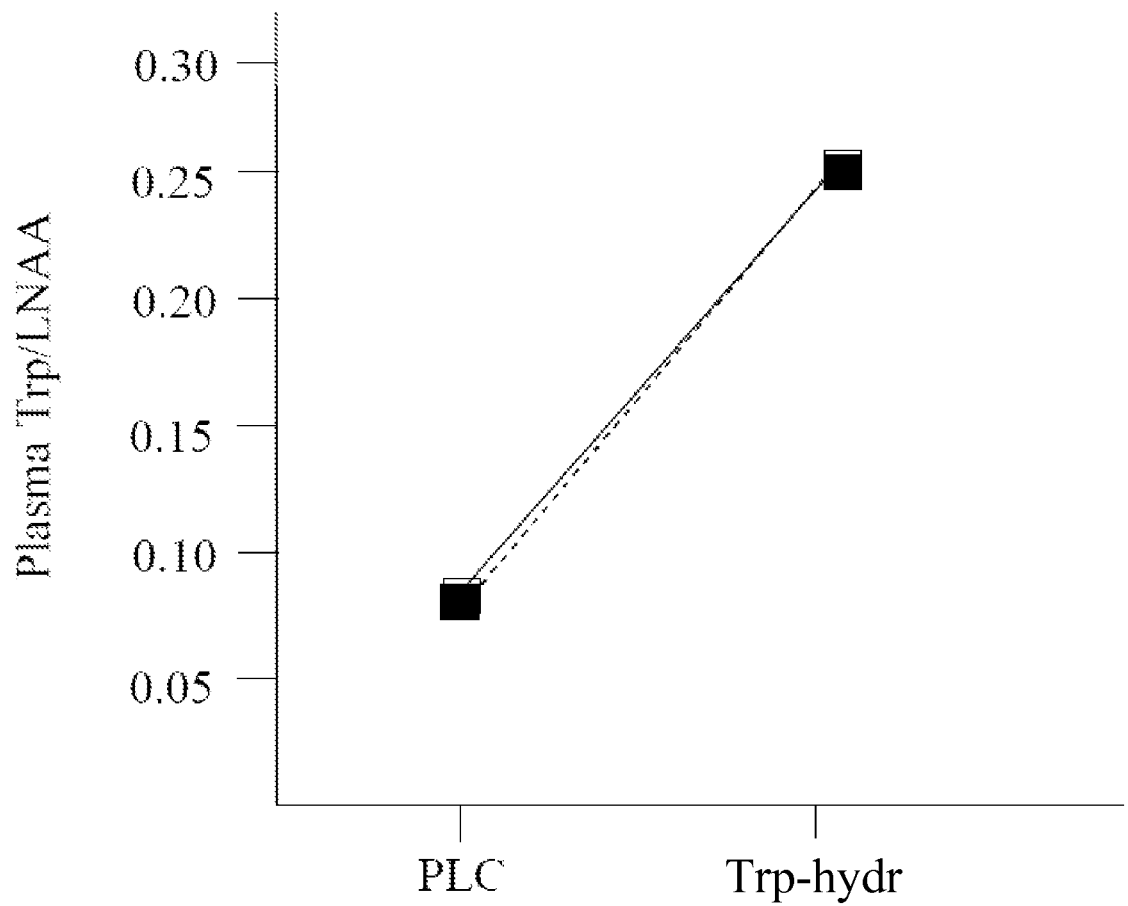

FIG. 6. Plasma Trp/LNAA ratios (µmol/1) following ingestion of placebo (plc) or the lysozyme hydrolysate (Trp-hydr) of the experiment described in Example 9. Black symbols: stress-susceptible subjects; open symbols: stress-resistant subjects.

Figure 7:
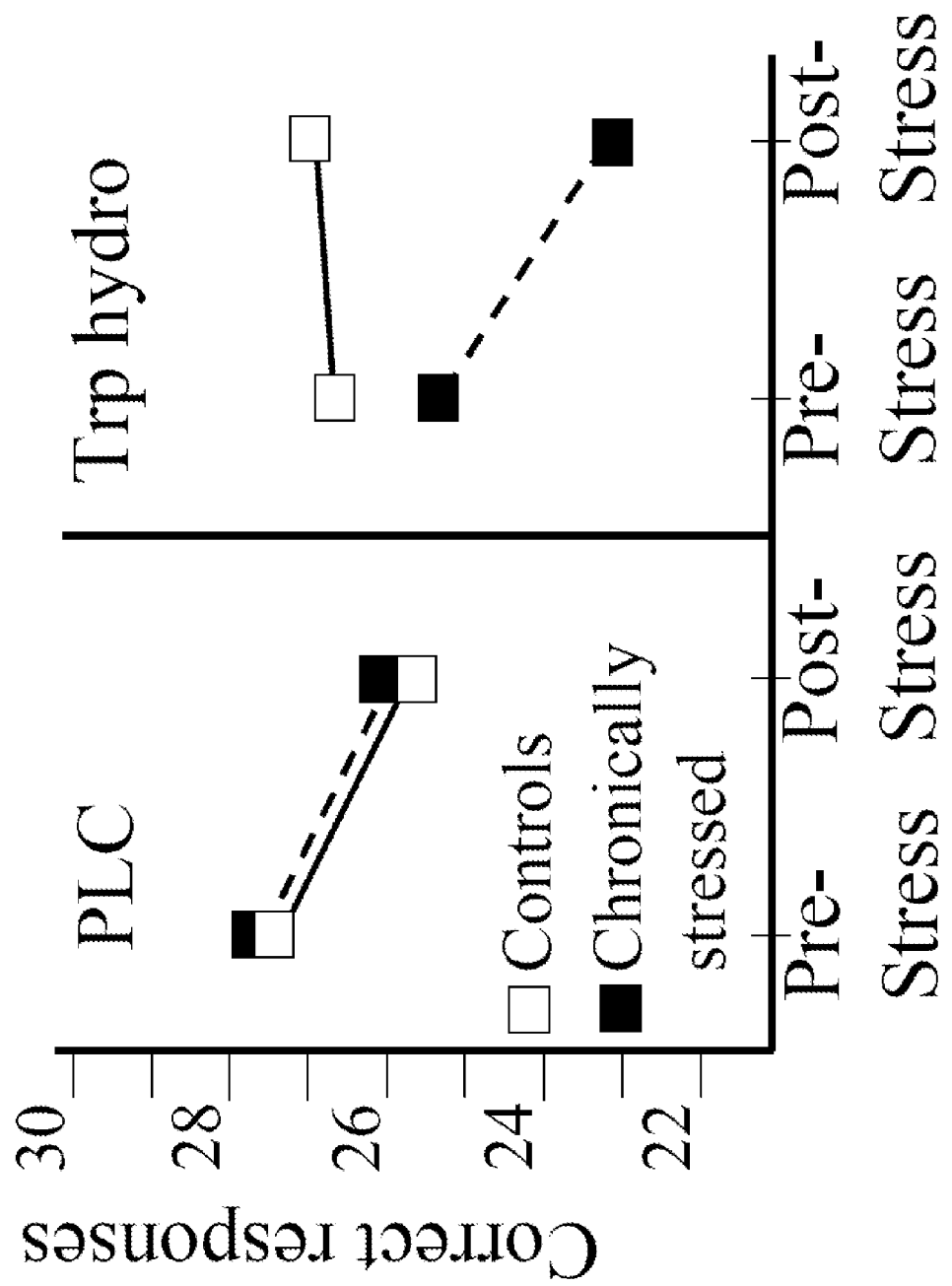

FIG. 7. Results of the Mackworth Clock Test carried out as described in Example 9. The number of correct responses (vertical axis) after consumption of placebo (plc; left-hand panel) or Trp-rich hydrolysate (Trp-hydr; right-hand panel), before (Pre-stress) or after (Post-stress) the arithmetic task. Black symbols: stress-susceptible subjects; open symbols: stress-resistant subjects. Since different intervention products were given on separate days, relevant comparisons may only be made between pre-stress and post-stress conditions within the same treatment and day.

Figure 8:
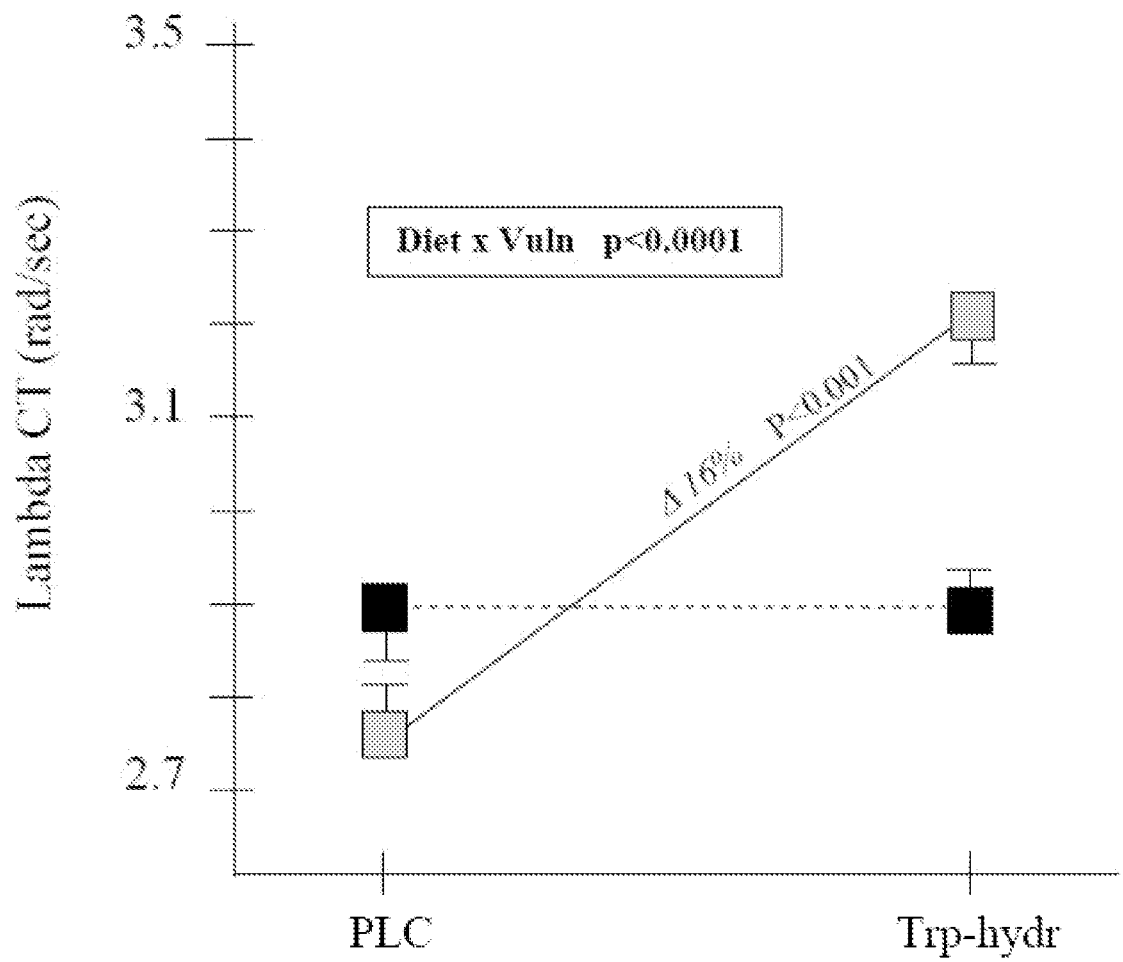

FIG. 8. Results of the Critical Tracking Task carried out as described in Example 9. Lambda CT (indicating the final level of complexity that is reached by the subjects) is expressed after intake of placebo (plc) or Trp-rich hydrolysate (Trp-hydr). Black symbols: stress-susceptible subjects; grey symbols: stress-resistant subjects.

Figure 9:
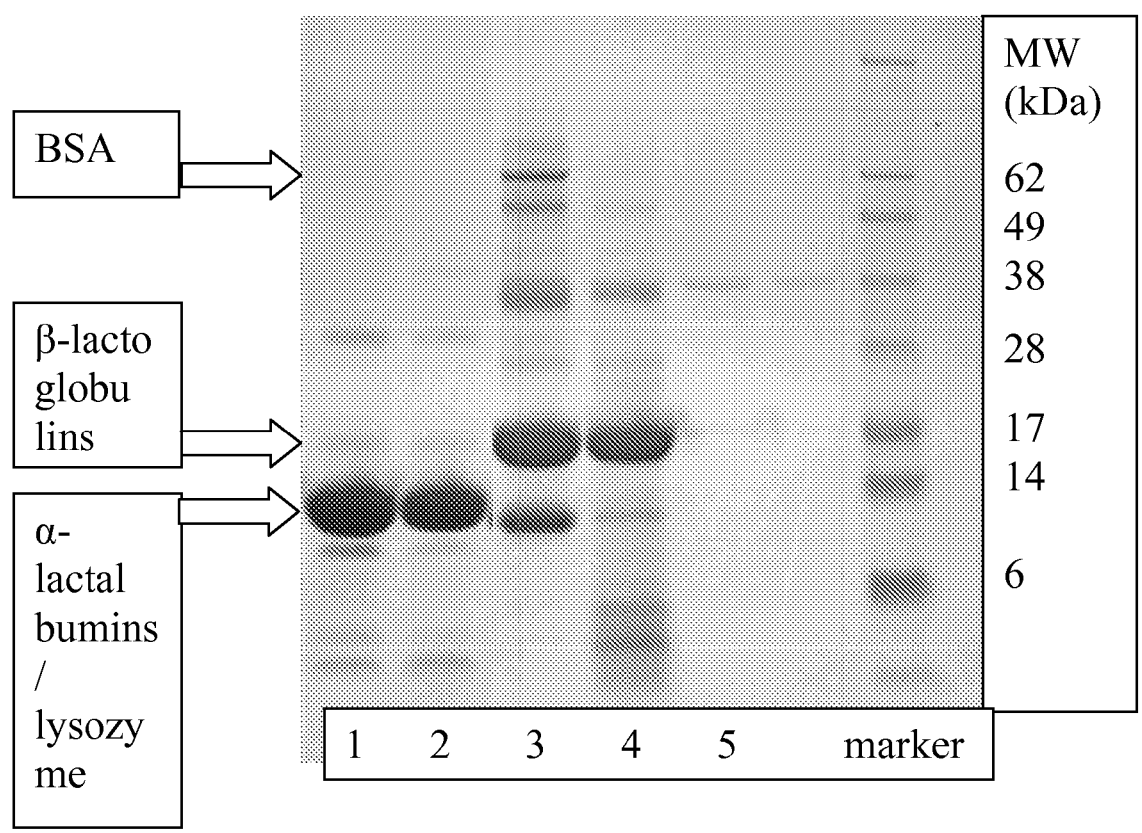

FIG. 9. SDS-PAGE of lysozyme and whey proteins incubated with pepsin under acid pH conditions.

Lane 1: lysozyme as such; lane 2: lysoyme after pepsin digestion; lane 3: whey protein as such; lane 4: whey protein after pepsin digestion; lane 5: pepsin as such.

Figure 10:
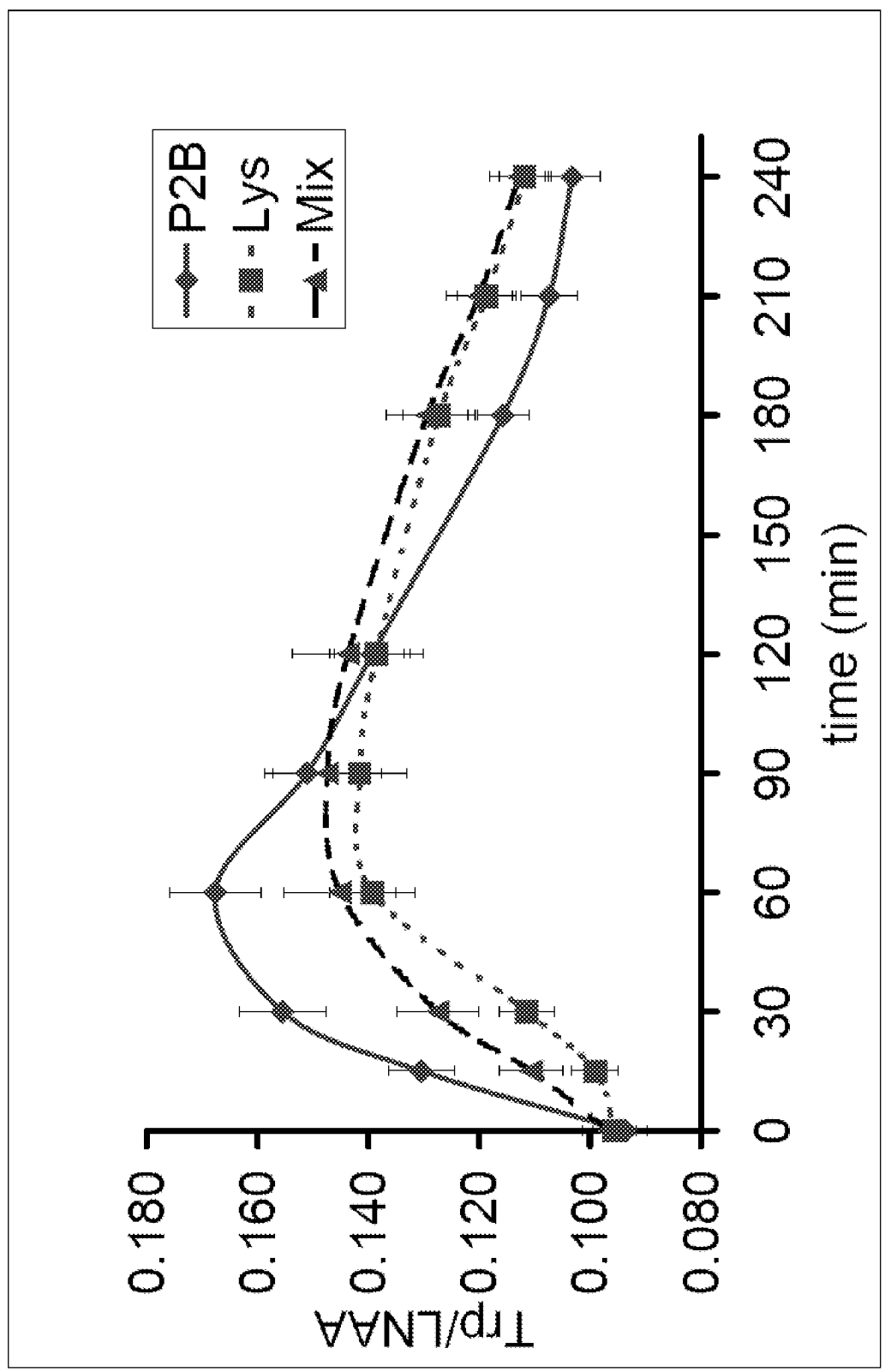

FIG. 10. Kinetics of the plasma Trp/LNAA ratios upon consumption of a product hydrolysed lysozyme (P2B=diamonds), intact lysozyme (Lys=squares), and a mix of intact and hydrolysed lysozyme (Mix=triangles). All three treatments have the same Trp content. Noteworthy is that all three products produce exactly the same "area-under-the-curve" values indicating that lysozyme hydrolysate as well as the intact lysozyme molecule are completely digested and taken up into the blood.

MATERIALS AND METHODS

Materials

Subtilisin under the commercial name of "Protex 6L" was obtained from Genencor (Leiden, The Netherlands), pepsin from Sigma and the mixture of trypsin/chymotrypsin (Porcine PEM) from Novozymes (Bagsvaerd, Denmark). Lysozyme was obtained either as Delvozyme L (22% dry matter) or as the dry Delvozyme G granulate from DSM Food Specialities (Delft, The Netherlands).

Casein hydrolysate ("REF") was obtained essentially as described by Edens et al (J Agric Food Chem, 53(20)7950-7957, 2005). Sodium caseinate was extensively hydrolysed with Protex 6L and, after lowering the pH to 4.5, with a proline specific endoprotease to reach a DH>20%. Following ultrafiltration, the permeate was heat treated to inactivate any remaining enzymatic activities and finally spray dried. Intact alpha-lactalbumin ("ALAC") was obtained as "Biopure" (>90% alpha-lactalbumin) from Davisco Foods International, Inc. (Le Seuer, Minn.); tryptophan-enriched lysozyme hydrolysate ("WEPS") was obtained as described in Example 4; the synthetic Ser-Trp dipeptide ("SYN") was obtained as described in Example 5; pure L-tryptophan ("TRP") was obtained as L-tryptophan −400 from Orthica, Almere, The Netherlands.

Test for Protease Resistancy of Tryptophan-Containing Polypeptides, Especially Intact proteins To test its digestibility in the human stomach, a 5% (w/w) solution of the intact protein was incubated with pepsin (Sigma; 1% w/w pepsin to intact protein) for 2 hours at 37 degrees C. in a Mc Ilvane buffer (0.2 M citric acid plus Na2HPO4) pH 4.0. The degree of protease resistance is defined as the percentage of the protein that is not affected by the pepsin incubation. "Not affected" meaning that the molecular weight of the protein has not changed as a result of the pepsin incubation; "percentage of the protein" meaning the area under the curve after digestion times 100, divided by the area under the curve prior to digestion; "area under the curve" is the area of the protein having the initial molecular weight as provided by the quantitative analysis method used (see further). Molecular weights are compared according to SDS-PAGE followed by staining according to the protocol specified hereunder. After staining of the gel, a digital image is prepared using the OptiGo imaging system (Isogen Life Science; www.isogen-life-science.com) followed by the quantitative analysis of selected protein bands using Totallab TL 100, version 2006 software (Nonlinear Dynamics Ltd; www.nonlinear.com) running under Windows XP. A protein is protease resistant according to the present text if more than 50% of the protein with the original molecular weight is still present after pepsin incubation.

SDS-PAGE

The purity of the lysozyme preparations used was checked by SDS-PAGE. All materials used for SDS-PAGE and staining were purchased from Invitrogen (Carlsbad, Calif., US). Samples were prepared using SDS buffer according to manufacturers instructions and separated on 12% Bis-Tris gels using MES-SDS buffer system according to manufacturers instructions. Staining was performed using Simply Blue Safe Stain (Collodial Coomassie G250). Prior to hydrolysis the lysozyme appeared as a single band with a molecular weight of approx. 14 kDa on the gel.

LC/MS/MS Analysis

HPLC using an ion trap mass spectrometer (Thermo Electron, Breda, the Netherlands) coupled to a P4000 pump (Thermo Electron, Breda, the Netherlands) was used to determine the presence of tryptophan containing peptides (mainly di- and tri peptides) in the enzymatic protein hydrolysates produced by the process according to the invention. The peptides formed were separated using an Inertsil 3 ODS 3, 3 μm, 150*2.1 mm column (Varian Belgium, Belgium) in combination with a gradient of 0.1% formic acid in Milli Q water (Millipore, Bedford, Mass., USA; Solution A) and 0.1% formic acid in acetonitrile (Solution B) for elution. The gradient started at 100% of Solution A, kept here for 10 minutes, increasing linear to 20% B in 25 minutes and immediately going to the starting conditions, and kept here 15 minutes for stabilization. The injection volume used was 50 microliters, the flow rate was 200 microliter per minute and the column temperature was maintained at 55° C. The protein concentration of the injected sample was approx. 50 micrograms/milliliter. Identification of the peptides of interest is based on the retention time, protonated molecule and by using dedicated MS/MS for the peptides of interest, using optimal collision energy of about 30%. Quantification of specific tryptophan containing peptides is performed by using an external standard method.

The tetra peptide VVPP (M=410.2) was used to tune for optimal sensitivity in MS mode and for optimal fragmentation in MS/MS mode, performing constant infusion of 5 μg/ml, resulting in a protonated molecule in MS mode, and an optimal collision energy of about 30% in MS/MS mode, generating a B- and Y-ion series.

Prior to LC/MS/MS the enzymatic protein hydrolysates were centrifuged at ambient temperature and 13000 rpm for 10 minutes and the supernatant was diluted 1:100 with demineralised water filtered through Millipore water filtration equipment (MilliQ water).

Amino Acid Analyses

The amino acid profiles in plasma were analyzed by HPLC according to van Eijk et al (J. Chromatogr. 1993:620:143-148) as described in Example 6 or Example 11.

Other amino acid analyses were carried out according to the PicoTag method as specified in the operators manual of the Amino Acid Analysis System of Waters (Milford Mass., USA). To that end samples were dried and directly derivatised using phenylisothiocyanate. The derivatised amino acids present were quantitated using HPLC methods as described. As during the usual acid hydrolysis Trp and Cys are destroyed, special methods were used to quantitate these two amino acids. To prevent Cys degradation during hydrolysis, this amino acid is first oxidized to cysteic acid using hydrogen peroxide and then quantitated. The analysis of tryptophan is based on a slightly modified Waters procedure. In this procedure an aliquot of the peptide solution is dried under vacuum and then hydrolysed during 1 hour at 150 degrees C. under nitrogen in 4M methane sulphonic acid containing 0.2% tryptamine. The reaction product is directly quantitated using HPLC equipped with an Alltech Altima C18 column and fluorescence detection.

Degree of Hydrolysis

The Degree of Hydrolysis (DH) as obtained during incubation with the various protolytic mixtures was monitored using a rapid OPA test (Nielsen, P. M.; Petersen, D.; Dambmann, C. Improved method for determining food protein degree of hydrolysis. *Journal of Food Science* 2001, 66, 642-646).

Kjeldahl Nitrogen

Total Kjeldahl Nitrogen was measured by Flow Injection Analysis. Using a Tecator FIASTAR 5000 Flow Injection System equipped with a TKN Method Cassette 5000-040, a Pentium 4 computer with SOFIA software and a Tecator 5027 Autosampler the ammonia released from protein containing solutions was quantitated at 590 nm. A sample amount corresponding with the dynamic range of the method (0.5-20 mg N/l) was placed in the digestion tube together with 95-97% sulphuric acid and a Kjeltab subjected to a digestion program of 30 minutes at 200 degrees C. followed by 90 minutes at 360 degrees C. After injection in the FIASTAR 5000 system the nitrogen peak is measured from which the amount of protein measured can be inferred.

Molecular Weight Distribution of Peptides and Proteins Present in Hydrolysates.

Analysis of the peptide size distribution of protease treated protein samples was done on an automated HPLC system equiped with a high pressure pump, an injection device able to inject 10-100 microliter sample and a UV detector able to monitor the column effluent at 214 nm.

The column used for this analysis was a Superdex Peptide HR 10/300 GL (Amersham) equilibrated with 20 mM Sodium Phosphate/250 mM Sodium Chloride pH 7.0 buffer. After injecting a sample (typically 50 microliter) the various components were eluted from the column with buffer in 90 min at a flow rate of 0.5 ml/min. The system was calibrated using a mixture of cytochrome C (Mw 13 500 Da), aprotinin (Mw 6510 Da) and tetra-glycine (Mw 246 Da) as molecular weight markers.

The following Examples illustrate the invention further.

EXAMPLES

Example 1

Hen Egg Lysozyme is not Cleaved by Either Pepsin or Trypsin/Chymotrypsin

To test its digestibility in the human gastrointestinal tract, hen egg lysozyme was incubated in vitro with pepsin as well as with a mixture of trypsin and chymotrypsin. Both incubations were carried out under pH conditions that are prevalent in the stomach (pepsin) and duodenum (trypsin/chymotrypsin). To that end, a 5% (w/w) lysozyme solution was incubated with the enzymes (1% w/w enzyme to lysozyme protein) for 2 hours at 37 degrees C. To prevent major pH changes as the result of the ongoing protein hydrolysis, incubation was carried out in a Mc Ilvane buffer (0.2 M citric acid plus Na2HPO4). The low DH's values that are obtained after the two hours hydrolysis at 37 degrees C. (see Table 1), demonstrate that the lysozyme molecule cannot be degraded under conditions that mimic digestion conditions in the stomach and in the duodenum and jejunum because successful proteolysis can be expected to lead to a DH value of at least 10%. Therefore, tryptophan residues present in the intact hen egg lysozyme molecule will not be liberated in the gastrointestinal tract hereby implying that tryptophan molecules present in intact hen egg lysozyme cannot contribute to plasma tryptophan levels shortly after consumption.

TABLE 1

Lysozyme hydrolysis by pepsin and a trypsin/chymotrypsin mixture

| Enzyme | pH start | pH end | DH start (%) | DH end (%) |
|---|---|---|---|---|
| Pepsin | 2.8 | 2.4 | =0 | 2.4 |
| Pepsin | 3.6 | 3.2 |  | <1 |
| Pepsin | 4.6 | 4.3 |  | 1.0 |
| Trypsin/chymotrypsin | 4.6 | 4.3 |  | <1 |
| Trypsin/chymotrypsin | 5.9 | 5.5 |  | <1 |
| Trypsin/chymotrypsin | 7.2 | 7.0 |  | 1.3 |

Example 2

Hen Egg Lysozyme is Efficiently Cleaved by Subtilisin at Elevated pH Values

To test the susceptibility of lysozyme to enzyme hydrolysis under non-physiological pH and enzyme conditions, a lysozyme solution was incubated in vitro with a microbial subtilisin (EC 3.4.21.62) under alkaline pH conditions. To that end, a 5% (w/w) lysozyme solution was incubated at pH 7.0, 8.0 and 9.0 with 12.5 microliter of Protex 6 L.per gram lysozyme protein present. The incubation was carried out for 3 hours at 60 degrees C. with a constant adjustment of the pH using 1M NaOH. The incubations yielded slightly turbid solutions without any significant precipitates. After a heating step to inactivate the subtilisin activity, the DH values of the various incubations were measured according to the protocol described in the Materials & Methods section. In contrast with the results obtained under physiological conditions (see Example 1), alkaline incubation conditions using subtilisin result in complete lysozyme hydrolysis. The pH 7.0 incubation yielded a DH of 6.3, the pH 8.0 incubation a DH of 11.2 and the pH 9.0 incubation a DH of 16.4. A subsequent SDS-PAGE analysis of the reaction products, indicated that the whole lysozyme molecule was degraded i.e. no large molecular weight fragments survived the subtilisin incubation. Furthermore, HPLC analysis of the hydrolysate on a Crownpak CR+ column (Daicel) revealed that no significant racemisation of tryptophan containing peptides took place, not even after prolonged heating at pH 9.0.

Example 3

Hydrolysing Lysozyme Using Protex and Identity of the Peptides Formed

A solution containing 10% (w/w) pure lysozyme was adjusted to pH 8.2 using NaOH and heated to 52 degrees C. Hydrolysis was started by adding 25 microliter of Protex/g of protein present. Under continuous stirring and maintaining the pH at 8.2, the hydrolysis was continued for 5.5 hours to yield an almost clear solution without a visible precipitate. After a heating step to inactivate the Protex activity, a sample was taken for DH analysis. The DH of the solution turned out to be almost 30%. The heat treated solution was ultrafiltered over a 10 kDa filter to yield a completely clear liquid. This clear liquid was used for LC/MS analysis, for molecular weight distribution of peptides and proteins present as well as for ion exchange chromatography.

To get an impression of the molecular weight distribution of peptides and proteins present, the clear liquid was subjected to a molecular size analysis as described in the Materials & Methods section. The results obtained (see FIG. 3), clearly indicate that almost all peptides incorporating amino acids with an aromatic side chain (i.e. tryptophan, tyrosine and phenylalanine) have a molecular weight below 500 kDa. In view of the high molecular weight of these amino acids, the implication is most of these small peptides are either tri- or dipeptides.

LC/MS analysis was carried out according to the procedure as described in the Materials & Methods section. By selecting for those peptides containing a tryptophan ("W"), peptides AW, GNR, WIR, NAW, WVA, VAW, AWR, SLGNW and minor quantities of WW and SRWW could be detected. The level of free tryptophan in the hydrolysate after incubation was established to represent less than 1% of the total (lysozyme) tryptophan present.

As di- and tripeptides are readily absorbed by peptide transporters present in the intestinal wall, there is little doubt that tryptophan residues present in such peptides will be rapidly absorbed and lead to increased plasma tryptophan levels upon oral intake of the present lysozyme hydrolysate.

Example 4

Increasing the Tryptophan Content of the Hydrolysate

Lysozyme incorporates a surprising high amount of the basic arginine and lysine residues. Furthermore the lysozyme molecule incorporates a significant number of the acid glutamate and aspartate residues. This data has been used to devise an innovative and elegant purification route towards hydrolysates featuring high Trp/LNAA ratios. Essential requirement for this purification route is, however, that only very few of the tryptophan residues show up in peptides also containing either an arginine or lysine residue or a glutamate or aspartate residue. As shown in Example 3, the specific hydrolysis route used here yields only few trytophan containing peptides containing an arginine residue and no peptides containing a lysine, glutamate or aspartate residue. Theory predicts that a maximal charge difference between peptides with and without a glutamate or aspartate residue can be achieved around pH 3. A maximal charge difference between peptides with and without an arginine or lysine residue, can be achieved around pH 5.

To illustrate the selective power of this approach, a lysozyme hydrolysate was prepared according to the procedure specified in Example 3. Then, the pH of the hydrolysate was adjusted to pH 3.1 using acetic acid and approximately 0.5 gram of protein was applied to a 15 ml bed volume of SP Sepharose FF (GE Healthcare, Diegem, Belgium) column equilibrated with 20 mm sodium citrate pH 3.1. After washing the column with one column volume of the sodium citrate buffer to remove the majority of the peptides incorporating a glutamate or aspartate, the elution buffer was changed to a 20 mm sodium citrate buffer pH 5.1. During washing of the column with three column volumes of the latter buffer, a range of tryptophan containing peptides was eluted. According to LC/MS analysis, the dipeptide AW was present in large amounts as well as the tripeptides GNR, NAW, WVA, VAW and a small amount of the pentapeptide SLGNR. Amino acid analysis of the various pH 5.1 fractions showed that selective pooling yielded a solution having a molecular Trp/LNAA ratio of 1.75 and a tryptophan yield of almost 30%. A less selective pooling yielded a solution with a molecular Trp/LNAA ratio of 0.4 and a tryptophan yield of 70%. Subsequently, the column was washed with three column volumes 20 mM sodium citrate pH 7.1. According to the LC/MS data, this step eluted arginine containing peptides WIR, AWIR and, surprisingly, peptide WW. A final washing of the column with 1 M of NaOH, water and 1M of acetic acid prepared the column for a next run.

Example 5

Chemical Synthesis of Dipeptide Ser-Trp

The dipeptide Ser-Trp was synthesized according to standard peptide technology. In a first step Z-Ser-OH and Trp-OMe were coupled via the carbonic anhydride methodology (*J. Am. Chem. Soc.* 1967, 5012) to yield the protected dipeptide Z-Ser-Trp-OMe. To that end Trp-OMe.HCl was suspended in tetrahydrofuran (THF) and subsequently N-methylmorpholine (NMM) was added. The mixture was stirred for one hour and subsequently added to a solution of Z-Ser in tetrahydrofuran/dimethylformamide (THF/DMF). A second equivalent of NMM was added and the mixture was cooled to −15° C. Isobutyl chloroformate is added at such a rate that the internal temperature does not exceed −15° C. Subsequently, the mixture was stirred for 3 hours, the temperature was allowed to rise to ambient temperature and the precipitated NMM.HCl was removed by filtration. The filtrate was kept at 4° C. overnight after which any additional precipitate was filtered and the filtrate is concentrated in vacuo. The residue was purified by column chromatography ($SiO_2$, ethyl acetate/heptane). The combined fractions were concentrated, washed with water to remove any remaining DMF and concentrated in vacuo.

In a second step, enzymatic hydrolysis of Z-Ser-Trp-OMe was accomplished using Alcalase 2.5 L DX (*Int. J. Peptide Protein Res.* 1990, 52) and subsequent catalytic hydrogenolysis provided the desired peptide as an off-white solid. To that end the purified Z-Ser-Trp-OMe was dissolved in tBuOH and water and Alcalase 2.5 L DX (Novozymes, Bagsvaerd, Denmark) was added. The mixture was stirred until (almost) all starting material was consumed. The mixture was then concentrated in vacuo and the residue taken up in water of pH 7. The aqueous mixture was extracted with ethyl acetate to remove any remaining starting material and subsequently the aqueous phase was acidified. The desired product, i.e. Z-Ser-Trp-OH, was isolated by extraction with ethyl acetate; the extract was dried over sodium sulphate and concentrated in vacuo.

In a third step, dipeptide Ser-Trp-OH was obtained. To that end the concentrated Z-Ser-Trp-OH was dissolved in MeOH and water (1:1), Pd/C was added and the mixture was stirred under a postive hydrogen atmosphere (5 bar). Upon completion of the reaction, the catalyst plus the majority of the product was removed by filtration and the filtrate discarded. The filter was washed extensively with milliQ water and the filtrate concentrated in vacuo, yielding the dipeptide Ser-Trp-OH as a white to off-white solid. Additional purification was achieved by stirring the product in a mixture of acetone-water and isolation of the peptide by filtration. This yielded a product suitable for oral consumption.

Example 6

Effects of Different Tryptophan Sources on Plasma Trp/LNAA Ratios and Mood in Healthy Volunteers The aim of the present study was to investigate in healthy volunteers plasma Trp/LNAA profiles and mood after the consumption of different tryptophan containing preparations. The following preparations were tested:
  intact alpha-lactalbumin (see Materials & Methods)
  hydrolyzed caseinate (DH>20%; see Materials & Methods)
  a Trp-enriched lysozyme hydrolysate with a high Trp/LNAA ratio (see Example 4)
  a synthetic SW dipeptide (Example 5)
  free L-tryptophan (see Materials & Methods).

Eighteen healthy students (9 males and 9 females: age between 18-30 years) participated in the study. Exclusion criteria for participation were chronic and current illness, history of psychiatric or medical illness, use of medication or drugs, alcohol consumption (>2 units/day), metabolic-, hormonal- or intestinal diseases and irregular diets or deviant eating habits (assessed by health and life-style questionnaires). Subjects participating in the experiment were in the normal range for the Body-Mass Index (BMI in $kg/m^2$ between 20-25) and female subjects are matched for contraception. Women participated during their mid-late follicular phase (day 4-10), while women using contraception participated when they actually used the contraception pill. Participants were non-smokers and did not use any alcohol before and during the study. All subjects participating in the experiment signed an Informed Consent Form. This study was conducted according to the EC principles of Good Clinical Practice (GCP) adopted by the $52^{nd}$ WMA General Assembly, Edinburgh, Scotland, October 2000.

Subjects were instructed to fast overnight; only water or tea without sugar was permitted. During five experimental morning sessions, subjects visited the laboratory to monitor plasma Trp/LNAA concentrations and mood following the intake of a drink containing different Trp or LNAA concentrations. The order of presentation of the various drinks was counterbalanced and the four experimental days were separated by a one-week period. On each experimental morning, a 312 ml drink was provided containing different tryptophan (Trp) or LNAA concentrations (Table 2). All drinks contained 0.10 g sweetener (acesulfame) and were filled up with plain water in order to reach 312 mL. A research assistant blind to the dietary conditions conducted the administration of the different drinks.

TABLE 2

Protein/amino acid composition of drinks used

| | Protein source | | | | |
|---|---|---|---|---|---|
| | Casein Hydrol. | Intact Alpha-lac | Trp-enhanced lysozyme hydrol. | Ser-Trp | Free L-Trp |
| Code used | REF | ALAC | WEPS | SYN | TRP |
| grams | 20 | 15 | 300 ml solution | 1.20 | 0.82 |
| Trp (g) | 0.40 | 0.80 | 0.80 | 0.80 | 0.80 |
| Trp/LNAA (molar) | 0.04 | 0.10 | 1.1 | ∞ | ∞ |

Blood samples were collected in duplicate before and 15, 30, 60, 90, 120, 180 and 210 minutes after ingestion in 5 ml vacutainer tubes containing sodium heparine and were then centrifuged at 5000 rpm for 5 min at 4° C. The resulting supernatants were mixed with sulfasalicyl acid (4 mg/100 microliter) and directly stored at −80° C. until analysis. Plasma amino acid analysis was conducted with HPLC, making use of a 2-3 μm Bischof Spherisorb ODS II column as described by van Eijk et al (J. Chromatogr. 1993:620:143-148). The plasma Trp/LNAA ratios were calculated by dividing the plasma molar tryptophan concentration by the sum of the plasma molar concentrations of the large neutral amino acids valine, isoleucine, leucine, tyrosine and phenylalanine. Statistical analysis took place by means of repeated measures multivariate and univariate analyses of variance (MANOVA and ANOVA) using the General Linear Model (GLM: SPSS 12.0 for Windows). All statistics were evaluated at a significance level of P=0.05.

Plasma Trp/LNAA Values

A first repeated measures analysis of variance with Condition and Time as within-subjects factors on the plasma Trp/LNAA ratio revealed a main significant effect of Time and Condition and a significant interaction Condition×Time. The highest significant increases in plasma Trp/LNAA ratio were found (see FIG. 1) after providing "SYN" (increase 263% after 60 min) and "WEPS" (increase 255% after 90 min). The increase in Trp/LNAA after these two products, was significantly faster and higher than after intake of either "TRP" (increase 191% after 120 min) or "ALAC" (increase 67% after 120 min). After consumption of "REF", there was a significant decline in Trp/LNAA starting 60 min until 210 min (−27%).

The 255% rise in Trp/LNAA as found with "WEPS" considerably exceeds the 50-70% increases as previously found with intact alpha-lactalbumin (Markus et al., 2000; Booij et al., 2006) and all earlier reported 20-45% increases with other foods like carbohydrates (Markus, 2003). While a 40-50% variation in plasma Trp/LNAA is thought to be sufficient to change Trp levels and 5-HT synthesis and release in the brain (Markus et al., 2000), this 255% rise is expected to cause a much larger rise in available brain Trp and 5-HT and therefore may also result in a greater release of functionally active brain 5-HT.

Profile of Mood States (POMS).

Mood changes of the various participants were measured using a paper-and-pencil version of the Dutch shortened version of the Profile of Mood States questionnaire (Wald and Mellenbergh, Ned Tijdschr Psycho) 1990:45:86-90) as a VAS scale ranging from 'strongly disagree' to 'strongly agree'. The POMS comprises five different subscales for mood; ranging from Anger, Depression, Fatigue and Tension that refer to a negative mood state, to Vigor concerning a positive mood.

Repeated measures analysis of variance with Condition and Time as within-subjects factors on the total mood scores revealed a significant effect of Time and a significant interaction of Condition×Time; indicating that mood changes across time significantly differed between conditions. Comparable improvements of mood were found 60 min after the intake of "WEPS" and "TRP", but only with "WEPS" mood further improved until 210 min after intake as compared with "TRP". In contrast, no mood changes were found after the intake of "REF" and "ALAC". The absence of a mood effect after intact alpha-lactalbumin is comparable with previous studies showing mild beneficial effects on mood after intact alpha-lactalbumin and only in stress-vulnerable subjects under acute stress exposure (Markus et al., 2000; Markus et al., 2000, Markus, 2003). Although mood also seemed to improve after intake "SYN", this effect was not significant in this experimental set up.

These current results suggest that a large 255% increase in plasma Trp/LNAA may be sufficient for an improved mood in normal non-stress-vulnerable subjects. Based on previous findings it is expected that these beneficial effects of the Trp-enhanced lysozyme hydrolysate on mood will be even greater in stress-vulnerable subjects under high mental stress conditions (Markus, 2003). Contrary to our expectations, there were no significant improvements in mood after intake of the synthetic dipeptide. This unexpected result may be attributable to the current experimental set up or to differences in tryptophan bioavailability from these various sources.

TABLE 3

Changes in plasma amino acid concentrations (μmol/l) in time after ingestion of casein hydrolysate ("REF"), intact alpha-lactalbumin ("ALAC") or Trp-enhanced lysozyme hydrolysate ("WEPS").

| Amino acid | Condition | Time (min) | | | | | | |
| --- | --- | --- | --- | --- | --- | --- | --- | --- |
| | | 0 | 30 | 60 | 90 | 120 | 180 | 210 |
| Isoleucine | REF | 0.07 | 0.10 | 0.18 | 0.15 | 0.12 | 0.09 | 0.08 |
| | ALAC | 0.08 | 0.12 | 0.20 | 0.22 | 0.18 | 0.12 | 0.11 |
| | WEPS | 0.07 | 0.09 | 0.09 | 0.14 | 0.09 | 0.08 | 0.09 |
| Leucine | REF | 0.12 | 0.19 | 0.31 | 0.26 | 0.22 | 0.17 | 0.16 |
| | ALAC | 0.13 | 0.22 | 0.37 | 0.38 | 0.28 | 0.21 | 0.20 |
| | WEPS | 0.13 | 0.14 | 0.14 | 0.13 | 0.13 | 0.13 | 0.14 |
| Phenylalanine | REF | 0.06 | 0.08 | 0.10 | 0.08 | 0.08 | 0.06 | 0.06 |
| | ALAC | 0.07 | 0.09 | 0.11 | 0.10 | 0.09 | 0.07 | 0.07 |
| | WEPS | 0.07 | 0.07 | 0.07 | 0.06 | 0.10 | 0.06 | 0.07 |
| Tyrosine | REF | 0.06 | 0.07 | 0.12 | 0.11 | 0.09 | 0.07 | 0.07 |
| | ALAC | 0.06 | 0.08 | 0.12 | 0.12 | 0.10 | 0.08 | 0.08 |
| | WEPS | 0.06 | 0.07 | 0.07 | 0.06 | 0.06 | 0.06 | 0.06 |
| Valine | REF | 0.24 | 0.28 | 0.45 | 0.42 | 0.38 | 0.32 | 0.30 |
| | ALAC | 0.26 | 0.30 | 0.38 | 0.42 | 0.35 | 0.29 | 0.28 |
| | WEPS | 0.26 | 0.27 | 0.25 | 0.25 | 0.25 | 0.25 | 0.26 |
| Tryptophan | REF | 0.06 | 0.07 | 0.08 | 0.08 | 0.07 | 0.06 | 0.05 |
| | ALAC | 0.07 | 0.09 | 0.18 | 0.23 | 0.19 | 0.13 | 0.12 |
| | WEPS | 0.07 | 0.13 | 0.21 | 0.23 | 0.20 | 0.14 | 0.13 |
| LNAA | REF | 0.52 | 0.67 | 1.14 | 1.01 | 0.86 | 0.73 | 0.65 |
| | ALAC | 0.60 | 0.82 | 1.14 | 1.22 | 1.10 | 0.86 | 0.82 |
| | WEPS | 0.62 | 0.60 | 0.65 | 0.60 | 0.68 | 0.55 | 0.64 |
| Trp/LNAA | REF | 0.11 | 0.09 | 0.08 | 0.08 | 0.08 | 0.08 | 0.08 |
| | ALAC | 0.12 | 0.12 | 0.15 | 0.18 | 0.2 | 0.18 | 0.17 |
| | WEPS | 0.11 | 0.19 | 0.36 | 0.39 | 0.35 | 0.25 | 0.22 |

TABLE 4

Changes in plasma amino acid concentrations (μmol/l) in time after ingestion of free L-Trp ("TRP") or the synthetic dipeptide SW ("SYN").

| Amino acid | Condition | Time (min) | | | | | | |
| --- | --- | --- | --- | --- | --- | --- | --- | --- |
| | | 0 | 30 | 60 | 90 | 120 | 180 | 210 |
| Isoleucine | TRP | 0.07 | 0.07 | 0.07 | 0.06 | 0.07 | 0.07 | 0.07 |
| | SYN | 0.06 | 0.07 | 0.06 | 0.06 | 0.06 | 0.06 | 0.07 |
| Leucine | TRP | 0.13 | 0.13 | 0.12 | 0.12 | 0.12 | 0.12 | 0.13 |
| | SYN | 0.11 | 0.14 | 0.12 | 0.12 | 0.12 | 0.12 | 0.13 |
| Phenylalanine | TRP | 0.07 | 0.07 | 0.06 | 0.06 | 0.06 | 0.06 | 0.06 |
| | SYN | 0.06 | 0.07 | 0.06 | 0.06 | 0.06 | 0.06 | 0.06 |
| Tyrosine | TRP | 0.06 | 0.06 | 0.06 | 0.05 | 0.06 | 0.05 | 0.05 |
| | SYN | 0.05 | 0.06 | 0.05 | 0.05 | 0.05 | 0.05 | 0.05 |
| Valine | TRP | 0.25 | 0.25 | 0.23 | 0.22 | 0.23 | 0.22 | 0.23 |
| | SYN | 0.21 | 0.26 | 0.22 | 0.22 | 0.22 | 0.21 | 0.23 |
| Tryptophan | TRP | 0.07 | 0.07 | 0.17 | 0.18 | 0.18 | 0.13 | 0.11 |
| | SYN | 0.06 | 0.13 | 0.21 | 0.18 | 0.15 | 0.11 | 0.10 |
| LNAA | TRP | 0.62 | 0.59 | 0.55 | 0.50 | 0.58 | 0.52 | 0.53 |
| | SYN | 0.50 | 0.58 | 0.48 | 0.47 | 0.45 | 0.48 | 0.54 |
| Trp/LNAA | TRP | 0.11 | 0.12 | 0.29 | 0.31 | 0.32 | 0.24 | 0.20 |
| | SYN | 0.11 | 0.22 | 0.40 | 0.37 | 0.31 | 0.22 | 0.19 |

Example 7

Large Scale Lysozyme Hydrolysis

In larger scale lysozyme hydrolysis procedures, essentially the procedure as described in Example 3 was followed with some minor modifications. A solution containing 7.3% (w/w) pure lysozyme was heated to 65 degrees C. after which the pH was adjusted to pH 8.2 using NaOH. Hydrolysis was started by adding 25 microliter of Protex 6 L/g dry matter. Under continuous stirring and maintaining the pH at 8.2 and the temperature at 53 degrees C., the hydrolysis was continued for 2 hours. Then the pH value was increased to 9.0 and incubation was pursued for another 3.5 hours to yield a solution with some precipitate. Then the pH of the solution was lowered to 4.5 and the solution was cooled to below 4 degrees C. To obtain a completely clear product, the liquid was filtered over a Z 2000 filter (Pall) and subsequently excess water and salt was removed via nanofiltration. The resulting concentrate was then subjected to an UHT treatment of 7 seconds at 120 degrees C., evaporated and finally spray dried to obtain the lysozyme hydrolysate in a dry form. The product thus obtained has a molar Trp/LNAA ratio of about 0.19.

Example 8

Preparing a Beverage Incorporating the Lysozyme Hydrolysate

The following recipe illustrates the preparation of an fat-free, lysozyme hydrolysate containing strawberry drink. To 10 grams of lysozyme hydrolysate powder (prepared according to Example 7), 40 grams of glucose, 2.4 grams of citric acid, 0.38 grams of malic acid, 0.15 grams of sucralose and 0.5 grams of strawberry flavor (Buteressence, Zaandam, The Netherlands) were added. This mixture of powders readily dissolves in 1 liter of water to obtain a ready-to-drink beverage with a high Trp/LNAA and a high Tyr/BCAA ratio. The powder mixture is suitable for e.g. sachet filling. Packaged liquid products can be produced using various known technologies.

Example 9

Effects of Lysozyme Hydrolysate on Post-stress Performance in Stress-susceptible and Stress-resistant Healthy Volunteers The aim of the present study was to compare the effects of a lysozyme hydrolysate prepared according to the procedure described in Example 7, with a placebo (casein protein hydrolysate; see Example 6) in terms of plasma Trp/LNAA levels and its consequences on post-stress performance tasks. The performance tests used are known to address "vigilance" and "eye-motor control" aspects of individuals.

Forty individuals, of which twenty males and twenty females, participated in the present study. Based on a pre-study questionnaire, one half of this group was classified as stress-resistant, the other half as stress-susceptible. The in- and exclusion criteria for the individuals as well as the general study conduct, were the same as described in Example 6. A flow diagram of the design of the study is given in FIG. 4 and a schematic of a typical study day is given in FIG. 5.

On the experimental mornings, subjects arrived fasted at the laboratory. Upon arrival, they were given either a drink containing the lysozyme hydrolysate, or the placebo i.e. the drink containing the casein hydrolysate. The composition of test drink and placebo drink is outlined in Table 5.

TABLE 5

Composition of drinks used.

| | Protein source | |
|---|---|---|
| | Casein hydrolysate | Lysozyme hydrolysate |
| abbreviation | plc | Trp-hydr |
| g powder/300 ml | 13.6 | 14.4 |
| Water | 286 g | 285 g |
| Sweetener | 0.1 g | 0.1 g |
| g Trp/300 ml | 0.4 | 0.8 |
| Trp/LNAA ratio (molar) | 0.04 | 0.19 |

Ninety minutes after consumption of the 300 ml drinks, a blood sample was taken to assess Trp/LNAA ratios (see Example 6). Subsequently, either the group of stress-resistant or the group of stress-prone subjects was exposed to a performance test followed by exposure to a stress. This stress consisted of an arithmetic task that had to be performed under noise stimulation. Subjects were led to believe that the presence or absence of the noise was depended on their performance in the test. In reality, the arithmetic tasks were manipulated in such a way that all subjects failed each trial. This set up is known to induce psychological stress and is perceived as highly uncontrollable (Peters, M. L., Godaert, G. L. R., Ballieux, R. E. et al. (1998). Cardiovascular and catecholamine response to experimental stress: effects of mental effort and controllability. Psychoneuroendocrinology. 23, 1-17). After the arithmatic task, the first performance test was repeated to quantify the effect of the stress on the performance under the influence of the blood Trp/LNAA ratios in force.

The performance tests carried out were the Mackworth Clock test (Mackworth, N (1948) The breakdown of vigilance during prolonged visual search. Quart J Exp Psych. 1, 6-21)) and the Critical Tracking Task (Jex H R et al., (1966) A "critical" tracking task for man-machine research related to the operator's effective delay time. NASA Contract Rep NASA CR.:1-105).

The Mackworth Clock Test is an extensively used test to measure "vigilance", alertness and concentration over a sustained period of time. Subjects are seated in front of a computer screen displaying a circular arrangement of 60 dots simulating the second marks on a clock. Dots are briefly illuminated in a clockwise rotation at a rate of one per 500 ms. Usually, the rotation proceeds with a single (one-dot) jump. Subjects were instructed that rarely, at irregular intervals, the target proceeds with a double (two-dot) jump by skipping one of the dots in the normal sequence. This should prompt the subjects to press a button as quickly as possible. A total of thirty such occasions were presented in the 45-minute test. Ten occasions occurred within each successive 15-minute period, with intervals ranging from 8 seconds to 7.2 minutes.

The Critical Tracking Task is used as a perceptual-motor performance task that measures the ability to control a displayed error signal in a first-order compensatory perceptual-motor coordination task. During this task, subjects have to control an unstable cursor on a computer screen by using a sensitive joystick. Errors will appear as horizontal deviations of the cursor from the midpoint on a horizontal linear scale. Subjects have to try to keep the unstable cursor in the center of the axis, to reduce deviations back to zero, by continuously making compensatory joystick movements. The frequency of cursor deviations increases as a stochastic, linear function of time, and therefore the subject is required to make compensatory movements with a progressively higher frequency. Also, the subject's compensatory responses increase in frequency with an increasing phase lag (a response adds to, rather than subtracts from, the error) and consequently control is lost. The frequency at which the subjects lose the control is the critical frequency. The test was performed five times; the average critical frequency was calculated without the lowest and highest score as the dependent variable of this test.

The plasma Trp/LNAA ratios determined 90 minutes after consumption of the drinks, revealed a significant effect (P<0.0001) on plasma Trp/LNAA ratio changes across the experimental conditions as applied. Ingestion of the lysozyme hydrolysate ("Trp-hydr") increased plasma Trp/LNAA value to 0.25 µmol/l. Ingestion of the casein hydrolysate ("plc") to a Trp/LNAA ratio of 0.08 µmol/l (FIG. 6) The values for each of the relevant amino acids are provided in Table 6.

TABLE 6

Amino acid concentrations (µmol/l) following ingestion of the placebo ("plc") or the lysozyme hydrolysate ("Trp-hydr").

|  | Tyr | Val | Ile | Phe | Leu | Trp | LNAA | Trp/LNAA |
| --- | --- | --- | --- | --- | --- | --- | --- | --- |
| plc | 90 | 315 | 107 | 63 | 168 | 60 | 744 | 0.082 |
| Trp-hydr | 73 | 266 | 120 | 58 | 152 | 167 | 670 | 0.250 |

After ingestion of the casein hydrolysate, the performance of both groups of individuals subjected to the Mackworth Clock Test was significantly impaired by exposure to stress. However, ingestion of the Trp-rich lysozyme hydrolysate prevented such an impaired performance in the stress-resistant group. Quite surprisingly, the Trp-rich hydrolysate did not prevent such an impaired performance in the stress-prone group. The data obtained are graphically represented in FIG. 7.

In the Critical Tracking Task, the lambda CT value indicates the final level of complexity that is reached by the subjects. The higher the lambda CT value, the better the control. The data obtained in the present experiment show that after exposure to stress, the lambda CT value was significantly higher when the Trp-rich hydrolysate was consumed. Among the stress-resistant individuals, a 16% increase could be scored relative to the placebo treatment. Quite surprisingly, also in this test, the lambda CT values in the stress-prone group showed no significant differences between the Trp-rich hydrolysate and the placebo.

Example 10

Protease Resistancy of Lysozyme and Alpha-lactalbumine

Together with beta-lactoglobulin, alpha-lactalbumin forms the major protein constituent of whey. Because of its high Trp/LNAA ratio, isolated alpha-lactalbumin fractions as well as alpha-lactalbumin hydrolysates have gained popularity for enhancing plasma tryptophan levels. Although alpha-lactalbumin and hen egg lysozyme both have unusually high Trp/LNAA ratios, in other respects these two molecules are quite different. According to the present application, a pepsin-resistant molecule with a high Trp/LNAA ratio is essential to maintain high plasma Trp/LNAA ratios longer term. Here we demonstrate that, unlike hen egg lysozyme, alpha-lactalbumin is not pepsin-resistant.

This was illustrated in the following experiment. To imitate conditions in the human stomach, 5% (w/w) solutions of lysozyme and whey protein (Bipro from Davisco) were incubated with pepsin (1% weight Sigma pepsin/weight lysozyme or whey proteins) for 2 hours at 37 degrees C. at pH 4 in a Mc Ilvane buffer (0.2 M citric acid plus Na2HPO4). After incubation both solutions were heated for 5 minutes at 80 degrees C. to terminate the reaction and small samples were subjected to SDS-PAGE (see Materials & Methods) to test the integrity of the various pepsin treated molecules.

FIG. 9 clearly illustrates that the quantity of intact hen egg lysozme is not significantly diminished by the incubation with pepsin under acid pH conditions. Of the whey proteins beta-lactoglobulin and alpha-lactoglobulin, beta-lactoglobulin remains largely intact but alpha-lactalbumin is almost completely degraded. The implication is that lysozyme as well as beta-lactoglobulin are "protease resistant" according to the test specified in the Materials & Methods section and that alpha-lactoglobulin is not "protease resistant". This finding illustrates that, unlike lysozyme, alpha-lactalbumin does-not qualify as a suitable source of polypeptide bound tryptophan. Despite the fact that beta-lactoglobulin is quite resistant to pepsin degradation, the molecule does not present a suitable tryptophan donor because of its very low Trp/LNAA ratio (0.04).

Example 11

Prolonging High Trp/LNAA Levels by Combining Lysozyme Hydrolysate with the Intact Molecule To demonstrate the advantage of a combination of the peptide-bound and polypeptide-bound tryptophan composition, a study was carried out involving 15 healthy individuals. Exclusion criteria were: chronic and current illness, at the discretion of the investigator; history of psychiatric disorders; use of selective serotonin reuptake inhibitors (SSRI); use of supplements targeting the central nervous system, such as supplements containing tryptophan, ephedrine, or St John's wort; egg allergy; drug abuse; participation in any other study involving investigational or marketed products concomitantly; intolerance to artificial sweeteners; any (history of) gastrointestinal disease that interferes with gastrointestinal function, at the discretion of the investigator; use of medication targeting the gastro-intestinal tract, such as antacids. Finally, for women, pregnancy or the use of a medically not accepted contraceptive method is an exclusion criterion as well.

All subjects participating in the experiment signed an Informed Consent Form.

Procedure

The study was performed according to a randomized, double-blind, crossover design with a washout period between the intake of the different treatments of three days at least.

During three experimental morning sessions, subjects visited the laboratory to monitor their plasma Trp/LNAA concentrations following the intake of a drink containing either 6 grams of intact lysozyme, 6 grams of lysozyme hydrolysate or 6 grams of a mixture of hydrolysate and intact product. The drinks were presented as sterile products in bottles with straws. The intact lysozyme was obtained as Delvozyme G. The hydrolysate was prepared as described in Example 7 and the mixture incorporated 30 mol percent of Trp as hydrolysate and 70 mol percent of Trp as intact lysozyme. All drinks contained 6 grams of lysozyme derived protein, 0.10 g sweetener (acesulfame) and were filled up by plain water in order to reach a 300 mL drink. A research assistant blind to the dietary conditions conducted the administration of the different drinks.

The subjects visited the site between 8 and 9 am, having fasted for at least 8 hours. A flexible canula for blood drawings was inserted in their non-dominant forearm. After ingestion of one of the three experimental drinks blood samples were taken before (t=0) and at t=15, 30, 60, 90 120, 180, 210 and 240 minutes after ingestion to measure plasma Trp/LNAA ratios. The intake of any food or drinks other than water was prohibited during these 240 minutes.

Plasma Measurements

Approx. 5 ml blood was collected in a lithium heparin blood tube, swung and put immediately on ice. The sample was subsequently centrifuged and 750 µl plasma was mixed with 5-SSA (4 mg/100 ml plasma).

These solutions were centrifuged at 13.000 RPM for 5 minutes and to 20 µl supernatant, 40 µl internal standard was added (160 mg Alpha-amino-adpic acid in 2 liter 1.2 mM HCl). 50 µl Borate buffer (included in Waters AccQ.Tag kit art nr.186003836), 40 µl 0.4M NaOH, and 20 µl reagent (included in Waters AccQ.Tag kit art nr.186003836) were added, mixed, and heated for 10 minutes at 55° C. Subsequently, 1 µl was injected onto the column and the analysis was proceeded as described by van Eijk et al (J. Chromatogr. 1993:620:143-148)

Results

The plasma Trp/LNAA ratio as a variable of time at the three different treatments is depicted in FIG. 10. All three treatments produced an increase of the Trp/LNAA ratio. The fastest (within 15 minutes) and steepest increase was observed following consumption of the lysozyme hydrolysate. Intact lysozyme produced a much slower increase of the Trp/LNAA ratio but also the decrease of the Trp/LNAA ratio over time was much slower. The mixture of intact and hydrolysed lysozyme produced an intermediate result.

In a "repeated measures" analysis, all three treatments show a significantly different treatment by time interaction (P<0.001), indicating that all three curves have significantly different shapes. Noteworthy is that all three products produce exactly the same "area-under-the-curve" values indicating that both lysozyme hydrolysate and intact lysozyme are completely digested and taken up into the blood.

Example 12

Combining Lysozyme Hydrolysate with Intact Lysozyme Improves the Taste of the Final Product Upon mixing the lysozyme hydrolysate with the intact molecule, a considerable change in the taste impression of the final product was noted. The following ratio's of hydrolysate and intact molecule were prepared in 4 gram/200 ml water end concentrations:

100% lysozyme hydrolysate
70% lysozyme hydrolysate –30% Lysozyme
50% lysozyme hydrolysate –50% Lysozyme
30% lysozyme hydrolysate –70% Lysozyme.

In all these combinations, the molar end concentrations of tryptophan were exactly the same. The hydrolysate was prepared as described in Example 7 and for the intact lysozyme the Delvozyme G granulated product was used.

Whereas the taste of the hydrolysate as such is slightly bitter, adding the non-hydrolysed product increasingly masks this bitter note and compensates it with a lingering, slightly sweet taste impression. Taste-wise an experienced test panel preferred the hydrolysate/intact lysozyme mixtures over the pure hydrolysate.

The invention claimed is:

1. A composition which comprises tryptophan, whereby 10 mol % to 90 mol % of the tryptophan is present as a peptide-bound tryptophan and/or free tryptophan and 10 mol % to 90 mol % of the tryptophan is present as polypeptide bound tryptophan in the form of intact lysozyme.

2. A composition according to claim 1, whereby more than 30 mol % of the peptide-bound tryptophan is present in the form of a di- or a tripeptide.

3. A composition according to claim 1, whereby more than 30 mol % of the polypeptide-bound tryptophan is present as intact lysozyme.

4. A composition according to claim 1, comprising at least one tryptophan-containing peptide which is water-soluble, or wherein the peptide-bound tryptophan fraction, which is water-soluble, has a Trp/Large Neutral Amino Acid (LNAA) ratio of at least 0.10.

5. A composition according to claim 1, which comprises the dipeptide AW or the tripeptide GNW.

6. A composition according to claim 1, comprising at least one tryptophan-containing peptide selected from the group consisting of di- or tripeptides, whereby the tryptophan-containing peptide is present in an amount of at least 5 mol% of the total amount of di- and tripeptides.

7. A composition according to claim 1, which comprises the water-soluble fraction of a lysozyme hydrolysate.

8. A food, pet food, feed, dietary supplement or nutraceutical comprising a composition according to claim 1.

* * * * *